US008288336B2

(12) United States Patent
Vitek et al.

(10) Patent No.: US 8,288,336 B2
(45) Date of Patent: *Oct. 16, 2012

(54) TREATMENT OF SUBARACHNOID HEMORRHAGE WITH APOE ANALOGS

(75) Inventors: Michael P. Vitek, Cary, NC (US); Daniel T. Laskowitz, Chapel Hill, NC (US)

(73) Assignee: Cognosci, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/270,105

(22) Filed: Oct. 10, 2011

(65) Prior Publication Data

US 2012/0053120 A1    Mar. 1, 2012

Related U.S. Application Data

(63) Continuation of application No. 12/023,288, filed on Jan. 31, 2008, now Pat. No. 8,034,762, which is a continuation-in-part of application No. 11/661,777, filed as application No. PCT/US2005/031431 on Sep. 2, 2005, now Pat. No. 7,947,645.

(60) Provisional application No. 60/608,148, filed on Sep. 9, 2004, provisional application No. 60/606,506, filed on Sep. 2, 2004, provisional application No. 60/606,507, filed on Sep. 2, 2004, provisional application No. 60/898,392, filed on Jan. 31, 2007.

(51) Int. Cl.
*A61K 38/00*    (2006.01)
*A61K 38/04*    (2006.01)
*C07K 5/00*    (2006.01)
*C07K 7/00*    (2006.01)
*C07K 16/00*    (2006.01)
*C07K 17/00*    (2006.01)

(52) U.S. Cl. .......... 514/1.1; 530/324; 530/325; 530/326

(58) Field of Classification Search .......... None
See application file for complete search history.

(56) References Cited

U.S. PATENT DOCUMENTS

| 4,902,505 | A | 2/1990 | Pardridge et al. | |
|---|---|---|---|---|
| 5,017,566 | A | 5/1991 | Bodor | |
| 5,114,956 | A | 5/1992 | Hoff | |
| 5,182,364 | A | 1/1993 | Dyer et al. | |
| 5,204,327 | A | 4/1993 | Kiyota et al. | |
| 5,473,039 | A | 12/1995 | Dyer et al. | |
| 5,604,198 | A | 2/1997 | Poduslo et al. | |
| 5,686,416 | A | 11/1997 | Kozarich et al. | |
| 6,245,751 | B1 | 6/2001 | Crutcher et al. | |
| 6,274,603 | B1* | 8/2001 | Poirier | 514/330 |
| 6,358,536 | B1* | 3/2002 | Thomas | 424/608 |
| 6,472,507 | B1 | 10/2002 | Fischer et al. | |
| 6,605,588 | B1 | 8/2003 | Lee et al. | |
| 6,890,902 | B2 | 5/2005 | Svendsen et al. | |
| 7,205,280 | B2* | 4/2007 | Laskowitz et al. | 514/17.8 |
| 7,319,092 | B2* | 1/2008 | Laskowitz et al. | 514/5.4 |
| 7,915,226 | B2* | 3/2011 | Laskowitz et al. | 514/21.4 |
| 8,034,762 | B2* | 10/2011 | Vitek et al. | 514/1.1 |
| 8,093,209 | B2* | 1/2012 | Laskowitz et al. | 514/1.4 |
| 2002/0164789 | A1 | 11/2002 | Laskowitz et al. | |
| 2004/0014652 | A1 | 1/2004 | Trouet et al. | |

FOREIGN PATENT DOCUMENTS

| WO | WO 92/10512 | 6/1992 |
|---|---|---|
| WO | WO 95/06456 | 3/1995 |
| WO | WO 97/14437 | 4/1997 |
| WO | WO 98/01101 | 1/1998 |
| WO | WO 99/08701 A1 | 2/1999 |
| WO | WO 99/45950 | 9/1999 |
| WO | WO 00/32236 * | 6/2000 |
| WO | WO 03/026479 A2 | 4/2003 |
| WO | WO 03/026479 A3 | 4/2003 |

OTHER PUBLICATIONS

Gebel et al. Intracerebral hemorrhage. Neurol Clin. 2000, vol. 18, No. 2, pp. 419-438.*

Towfighi et al. Treatment and Prevention of Primary Intracerebral Hemorrhage. Seminars in Neurology. 2005. vol. 25, Nol. 4, pp. 445-452.*

Aono, et al., "Protective Effects of Peptides Corresponding to the Receptor Binding Region of Apolipoprotein E on NMDA Excitotoxicity in Primary Neuronal-Glial Cultures", Trip Report: 31$^{st}$ Annual Meeting of the Society for Neuroscience, San Diego, California (Nov. 2001).

Barger, et al., "Microglial Activation by Alzheimer Amyloid Precursor Protein and Modulation by Apolipoprotein E", Nature 388: 878-881 (Aug. 1997).

Benazzouz, et al., "Riluzole Prevents MPTP-induced Parkinsonism in the Rhesus Monkey: A Pilot Study," *Eur. J. Pharmacol.* 284:299-307 (1995).

Bowie, et al., "Deciphering the message in protein sequences: tolerance to amino acid substitutions", Science, 247: 1306-1310 (1990).

Cardin, et al., "Inhibition of Lymphocyte Proliferation b Synthetic Peptides Homologous to Human Plasma Apolipoproteins B and E", Biochemical and Biophysical Research Communications, 154: 741-745 (Jul. 1998).

Champe, et al., "IV. Tertiary Structure of Globular Proteins," "V. Quaternary Structure of Proteins," "VI Denaturation of Proteins," and "VII. Protein Misfolding," pp. 18-21 in *Lippincott's Illustrated Reviews: Biochemistry*, 3rd Ed. Lippincott Williams & Wilkins, Philadelphia, Pennsylvania, USA (2005).

Chen, et al., "Motor and Cognitive Deficits in Apolipoprotein E Deficient Mice After Closed Head Injury," *Neuroscience* 80:1255-1262 (1997).

(Continued)

*Primary Examiner* — Marcela M Cordero Garcia
(74) *Attorney, Agent, or Firm* — Cooley LLP

(57) ABSTRACT

Novel ApoE peptide derivatives and ApoE-protein transduction domain conjugates are disclosed which are useful for treating disorders including subarachnoid hemorrhage, intracerebral hemorrhage, and intraventricular hemorrhage and other brain disorders. The invention encompasses methods for treating cerebral vasospasm by administration of at least one ApoE or ApoE mimetic peptide.

20 Claims, 7 Drawing Sheets

OTHER PUBLICATIONS

Christie, et al., "Expression of the Very Low-Density Lipoprotein Receptor (VLDL-r), an Apolipoprotein-E Receptor, in the Central Nervous System and in Alzheimer's Disease", Journal of Neuropathology and Experimental Neurology, 55(4): 491-498 (1996).

Clay, et al., "Localization of a Domain in Apolipoprotein E with Both Cytostatic and Cytotoxic Activity", Biochemistry, 34: 11142-11151 (1995).

Crutcher, et al., "Neurite degeneration elicited by apolipoprotein E peptides", Experimental Neurology 130(1):120-126 (1994).

Dong, et al., "Enhanced binding activity of an apolipoprotein E mutant, APO E5, to LDL receptors on human fibroblasts", Biochemical & Biophysical Research Communications 168(2):409-414 (Apr. 1990).

Dong, et al., "Site-directed mutagenesis of an apolipoprotein E mutant, apo E5(Glu3—Lys) and its binding to low density lipoprotein receptors", Biochemical & Biophysical Research Communications 187(2):1180-1186 (Sep. 1992).

Dyer, et al., "A Synthetic Peptide Mimetic of Plasma Apolipoprotein E that Binds the LDL Receptor", Journal of Biological Chemistry, 266: 22803-22806 (Dec. 1991).

Dyer, et al., "Only Multimers of a Synthetic Peptide of Human Apolipoprotein E Are Biologically Active", Journal of Biological Chemistry, 266: 15009-15015 (1991).

Gao, et al., "A novel apoE-derived therapeutic reduces vasospasm and improves outcome in a murine model of subarachnoid hemorrhage", Neurocritical Care, 4:25-31 (2006).

Gordon, et al., "Derangement in Stress Response of Apolipoprotein E-deficient Mice," *Neuroscience Letters* 206:212-214 (1996).

Holtzman, et al., "Low density lipoprotein receptor-related protein mediates apolipoprotein E-dependent neurite outgrowth in a central nervous system-derived neuronal cell line", Proc. Natl. Acad. Sci. USA, 92: 9480-9484 (1995).

Innerarity, et al., "Binding of arginine-rich (E) apoprotein after recombination with phospholipid vesicles to the low density lipoprotein receptors of fibroblasts", Journal of Biological Chemistry 254(10):4186-4190 (1979).

International Search Report for PCT/US99/05221 (mailed Nov. 3, 1999).

Jordan, et al., "Isoform-Specific Effect of Apolipoprotein E on Cell Survival and β-Amyloid-induced Toxicity in Rat Hippocampal Pyramidal Neuronal Cultures,"*J. Neurosci.* 18:195-204 (1998).

Lalazar, et al., "Site-specific Mutagenesis of Human Apolipoprotein E", Journal of Biological Chemistry, 263: 3542-3545 (1988).

Lanterna, et al., "APOE influences vasospasm and cognition of non-comatose patients with subarachnoid hemorrhage", Neurology, 64:1238-1244 (2005).

Laskowitz, et al., "Endogenous apolipoprotein E suppresses LPS-stimulated microglial nitric oxide production", Neuroreport. 9(4):615-618 (1998).

Laskowitz, et al., "Apolipoprotein E and the CNS response to injury", Journal of Cerebral Blood Flow & Metabolism 18(5): 465-471 (1998).

Laskowitz, et al., "Apolipoprotein E suppresses glial cell secretion of TNF alpha", Journal of Neuroimmunology 76(1-2):70-74, (1997).

Laskowitz, et al., "Apolipoprotein E-deficient mice have increased susceptibility to focal cerebral ischemia", Journal of Cerebral Blood Flow & Metabolism 17(7):753-758 (1997).

Laskowitz, et al., "Downregulation of Microglial Activation by Apolipoprotein E and ApoE-Mimetic Peptide", Experimental Neurology, 167: 74-85 (2001).

Leung et al., "Apolipoprotein E genotype and outcome in aneurysmal subarachnoid hemorrhage", Stroke, 33:548-552 (2002).

Ludwig, "Supplementary European Search Report," 3 pages, from EP Appl. No. 02775888.7, European Patent Office, Munich, Germany (mailed Mar. 9, 2007).

Lynch et al., "APOE Genotype and an ApoE-mimetic Peptide Modify the Systemic and Central Nervous System Inflammatory Response", Journal of Biological Chemistry, 278(4): 48529-33 (2003).

Lynch et al., "A novel therapeutic derived from apolipoprotein E reduces brain inflammation and improves outcome after closed head injury", Experimental Neurology, 192:109-116 (2005).

Marzolo, et al., "Expression of α2-Macroglobulin Receptor/ Low Density Lipoprotein Receptor-Related Protein (LRP) in Rat Microglial Cells," Journal of Neuroscience Research, 60:401-411 (2000).

Mesis et al., "Dissociation between Vasospasm and Functional Improvement in a Murine Model of Subarachnoid Hemorrhage", Neurosurgical Foucs, 21: 1-7 (2006).

Mickle, et al., "Genotype-phenotype relationships in cystic fibrosis", Med. Clin. North Am., 84 (3): 597-607 (May 2000).

Misra, et al., "Apolipoprotein E and Mimetic Peptide Initiate a Calcium-Dependent Signaling Response in Macrophages", Journal Leukocyte Bio. 70: 677-683 (2001).

Mrak, et al., "Glial Cytokines in Alzheimer's Disease: Review and Pathogenic Implications", Hum. Pathol. 26: 816-823 (Aug. 1995).

Nosko et al.,"Nimodipine and chronic vasospasm in monkeys: part 1. Clinical and radiological findings", Neurosurgery, 16:129-136 (1985).

Pardridge, "Chapter 12: Blood-brain barrier peptide transport and peptide delivery to the brain, Peptide-based drug design", Ed. Taylor et al., American Chemical Society, 265-296 (1995).

Petruk et al., "Nimodipine treatment in poor-grade aneurysm patients. Results of a multicenter double-blind placebo-controlled trial", Journal of Neurosurgery, 68:505-517 (1988).

Pickard et al., "Effect of oral nimodipine on cerebral infarction and outcome after subarachnoid hemorrhage: British aneurysm nimodipine trial", British Medical Journal, 298:636-642 (1989).

Tolar, et al., "Truncated Apolipoprotein E (ApoE) Causes Increased Intracellular Calcium and May Mediate ApoE Neurotoxicity," *J. Neuroscience* 19(16): 7100-7110 (1999).

Vitek, et al., "Modulation of nitric oxide production in human macrophages by apolipoprotein-E and amyloid-beta peptide", Biochemical & Biophysical Research Communications 240(2):391-394 (1997).

Volt, et al., Biochemistry, John Wiley & Sons, Inc., 126-128 and 228-234 (1990).

Weisgraber, et al., "The receptor-binding domain of human apolipoprotein E. Monoclonal antibody inhibition of binding", Journal of Biological Chemistry 258(20):12348-12354 (1983).

Yan, et al., "Two-amino acid molecular switch in an epithelial morphogen that regulates binding to two distinct receptors", Science, 290: 523-527 (2000).

Zielasek, et al., Advances in Neuroimmunology, 6 (2): 191-222 (1996).

Firuby, "Designing Peptide Receptor Agonists and Antagonists," Nature Reviews, Drug Discovery, vol. 1: 847-858, 2002.

Drin et al., "Studies on the Internalization Mechanism of Cationic Cell-penetrating Peptides," J. Biol. Chem., vol. 278: 31192-31201, 2003.

Binz et al., "Engineering novel binding proteins from nonimmunoglobulin domains," Nature Biotechnology. Oct. 2005. vol. 23, No. 10, pp. 1257-1268.

Gaggi et al., "Calcitonin enhances the effects of nimodipine on biogenic amines of rat brain," General Pharmacology: The Vascular System. vol. 23, Issue 3, May 1992, pp. 561-563.

Niall et al., "Amino acid sequence of salmon ultimobranchial calcitonin." PNAS, Oct. 1, 1969, vol. 64, No. 2, pp. 771-778.

\* cited by examiner

SEQUENCE LISTING

```
<160> NUMBER OF SEQ ID NOS: 58

<210> SEQ ID NO 1
<211> LENGTH: 17
<212> TYPE: PRT
<213> ORGANISM: Artificial Sequence
<220> FEATURE:
<223> OTHER INFORMATION: ApoE mimetic peptide COG133
<220> FEATURE:
<221> NAME/KEY: misc_feature
<222> LOCATION: (1)..(1)
<223> OTHER INFORMATION: Leucine may be biotinylated
<220> FEATURE:
<221> NAME/KEY: misc_feature
<222> LOCATION: (1)..(1)
<223> OTHER INFORMATION: Leucine may be acetylated
<220> FEATURE:
<221> NAME/KEY: misc_feature
<222> LOCATION: (17)..(17)
<223> OTHER INFORMATION: Leucine may be amidated

<400> SEQUENCE: 1

Leu Arg Val Arg Leu Ala Ser His Leu Arg Lys Leu Arg Lys Arg Leu
1               5                   10                  15

Leu

<210> SEQ ID NO 2
<211> LENGTH: 17
<212> TYPE: PRT
<213> ORGANISM: Artificial Sequence
<220> FEATURE:
<223> OTHER INFORMATION: Analog of COG133
<220> FEATURE:
<221> NAME/KEY: misc_feature
```

-continued

```
<222> LOCATION: (9)..(9)
<223> OTHER INFORMATION: Xaa is N-methylated leucine
<220> FEATURE:
<221> NAME/KEY: misc_feature
<222> LOCATION: (17)..(17)
<223> OTHER INFORMATION: Leucine may be amidated

<400> SEQUENCE: 2

Leu Arg Val Arg Leu Ala Ser His Xaa Arg Lys Leu Arg Lys Arg Leu
1               5                   10                  15

Leu

<210> SEQ ID NO 3
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (4)..(4)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 3

Ala Ser His Xaa Arg Lys Leu Arg Lys Arg Leu Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 4

Ala Ser Xaa Leu Arg Lys Leu Arg Lys Arg Leu Leu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
```

```
<221> NAME/KEY: misc_feature
<222> LOCATION: (12)..(12)
<223> OTHER INFORMATION: Leucine may be amidated

<400> SEQUENCE: 5

Asp Ser Xaa Leu Arg Lys Leu Arg Lys Arg Leu Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: COG432
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 6

Ala Ser His Leu Arg Lys Leu Xaa Lys Arg Leu Leu
1               5                   10

<210> SEQ ID NO 7
<211> LENGTH: 12
<212> TYPE: PRT
<213> ORGANISM: Artificial Sequence
<220> FEATURE:
<223> OTHER INFORMATION: COG1410
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 7

Ala Ser Xaa Leu Arg Lys Leu Xaa Lys Arg Leu Leu
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
```

<222> LOCATION: (14)..(14)
<223> OTHER INFORMATION: Xaa is amino iso-butyric acid
<220> FEATURE:
<221> NAME/KEY: misc_feature
<222> LOCATION: (15)..(15)
<223> OTHER INFORMATION: Leucine may be amidated

<400> SEQUENCE: 8

Asp Arg Xaa Ala Ser His Leu Arg Lys Leu Arg Lys Arg Xaa Leu
1 5 10 15

<210> SEQ ID NO 9
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (11)..(11)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 9

Asp Ser Xaa Leu Arg Lys Leu Arg Lys Arg Xaa Leu
1 5 10

<210> SEQ ID NO 10
<211> LENGTH: 15
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (11)..(11)
<223> OTHER INFORMATION: Xaa is amino iso-butyric acid
<220> FEATURE:
<221> NAME/KEY: misc_feature
<222> LOCATION: (15)..(15)
<223> OTHER INFORMATION: Leucine may be amidated

<400> SEQUENCE: 10

Asp Arg Xaa Ala Ser His Leu Arg Lys Leu Xaa Lys Arg Leu Leu
1 5 10 15

<210> SEQ ID NO 11
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)

-continued

```
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 11

Asp Ser Xaa Leu Arg Lys Leu Xaa Lys Arg Leu Leu
1               5                   10

<210> SEQ ID NO 12
<211> LENGTH: 15
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (6)..(6)
<223> OTHER INFORMATION: Xaa is amino iso-butyric acid
<220> FEATURE:
<221> NAME/KEY: misc_feature
<222> LOCATION: (15)..(15)
<223> OTHER INFORMATION: Leucine may be amidated

<400> SEQUENCE: 12

Asp Arg Xaa Ala Ser Xaa Leu Arg Lys Leu Arg Lys Arg Leu Leu
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (15)..(15)
<223> OTHER INFORMATION: Leucine may be amidated

<400> SEQUENCE: 13

Asp Arg Xaa Ala Ser His Leu Arg Lys Leu Arg Lys Arg Leu Leu
1               5                   10                  15

<210> SEQ ID NO 14
<211> LENGTH: 13
<212> TYPE: PRT
<213> ORGANISM: Artificial Sequence
<220> FEATURE:
<223> OTHER INFORMATION: Truncated analog of COG133
```

```
<220> FEATURE:
<221> NAME/KEY: misc_feature
<222> LOCATION: (1)..(1)
<223> OTHER INFORMATION: Cysteine may be acetylated
<220> FEATURE:
<221> NAME/KEY: misc_feature
<222> LOCATION: (4)..(4)
<223> OTHER INFORMATION: Xaa is amino iso-butyric acid
<220> FEATURE:
<221> NAME/KEY: misc_feature
<222> LOCATION: (9)..(9)
<223> OTHER INFORMATION: Xaa is amino iso-butyric acid
<220> FEATURE:
<221> NAME/KEY: misc_feature
<222> LOCATION: (13)..(13)
<223> OTHER INFORMATION: Leucine may be amidated

<400> SEQUENCE: 14

Cys Ala Ser Xaa Leu Arg Lys Leu Xaa Lys Arg Leu Leu
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Aspartic acid may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTH

```
<210> SEQ ID NO 17
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Methionine may be amidated

<400> SEQUENCE: 17

Ala Ser Xaa Leu Arg Lys Leu Xaa Lys Arg Leu Met
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Isoleucine may be amidated

<400> SEQUENCE: 18

Ala Ser Xaa Leu Arg Lys Leu Xaa Lys Arg Leu Ile
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
```

<223> OTHER INFORMATION: Alanine may be amidated

<400> SEQUENCE: 19

Ala Ser Xaa Leu Arg Lys Leu Xaa Lys Arg Leu Ala
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 20

Ala Ser Xaa Leu Arg Lys Leu Xaa Lys Ala Leu Leu
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (12)..(12)
<223> OTHER INFORMATION: Leucine may be amidated

<400> SEQUENCE: 21

Ala Ser Xaa Leu Arg Lys Leu Xaa Lys Xaa Leu Leu
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is nitroarginine
<220> FEATURE:
<221> NAME/KEY: misc_feature
<222> LOCATION: (12)..(12)
<223> OTHER INFORMATION: Leucine may be amidated

<400> SEQUENCE: 22

```
Ala Ser Xaa Leu Arg Lys Leu Xaa Lys Xaa Leu Leu
1               5                   10
```

<210> SEQ ID NO 23
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is homoarginine
<220> FEATURE:
<221> NAME/KEY: misc_feature
<222> LOCATION: (12)..(12)
<223> OTHER INFORMATION: Leucine may be amidated

<400> SEQUENCE: 23

```
Ala Ser Xaa Leu Arg Lys Leu Xaa Lys Xaa Leu Leu
1               5                   10
```

<210> SEQ ID NO 24
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is dimethyl arginine
<220> FEATURE:
<221> NAME/KEY: misc_feature

```
<222> LOCATION: (12)..(12)
<223> OTHER INFORMATION: Leucine may be amidated

<400> SEQUENCE: 24

Ala Ser Xaa Leu Arg Lys Leu Xaa Lys Xaa Leu Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 25

<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (9)..(9)
<223> OTHER INFORMATION: Xaa is azalysine
<220> FEATURE:
<221> NAME/KEY: misc_feature
<222> LOCATION: (12)..(12)
<223> OTHER INFORMATION: Leucine may be amidated

<400> SEQUENCE: 27

Ala Ser Xaa Leu Arg Lys Leu Xaa Xaa Arg Leu Leu
1 5 10

<210> SEQ ID NO 28
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (4)..(4)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 28

Ala Ser His Xaa Arg Lys Leu Xaa Lys Arg Leu Leu
1 5 10

<210> SEQ ID NO 29
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated -continued

```
<400> SEQUENCE: 29

Ala Ser Xaa Leu Arg Lys Leu Xaa Lys Arg Leu Xaa
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Leucine may be amidated

<400> SEQUENCE: 30

Ala Ser Xaa Leu Arg Lys Leu Xaa Lys Arg Xaa Leu
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 31

Ala Ser Xaa Leu Arg Lys Leu Xaa Lys Arg Xaa Xaa
1               5                   10

<210> SEQ ID NO 32
<211> LENGTH: 12
<212> TYPE: PRT
<213> ORGANISM: Artificial Sequence
```

```
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 32

Ala Ser Xaa Leu Arg Lys Leu Xaa Lys Xaa Leu Xaa
1               5                   10

<210> SEQ ID NO 33
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INF -continued

```
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 34

Ala Ser Xaa Leu Arg Lys Leu Xaa Lys Xaa Xaa Xaa
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is homoarginine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 35

Ala Ser Xaa Leu Arg Lys Leu Xaa Lys Xaa Leu Xaa
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
```

<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is homoarginine
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Leucine may be amidated

<400> SEQUENCE: 36

Ala Ser Xaa Leu Arg Lys Leu Xaa Lys Xaa Xaa Leu
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is homoarginine
<220> FEATURE:
<221> NAME/KEY: misc_feature
<222> LOCATION: (11)..(11)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 37

Ala Ser Xaa Leu Arg Lys Leu Xaa Lys Xaa Xaa Xaa
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid

```
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Leucine may be amidated

<400> SEQUENCE: 38

Ala Ser Xaa Leu Xaa Lys Leu Xaa Lys Arg Leu Leu
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
<220> FEATURE:
<221> NAME/KEY: misc_feature
<222> LOCATION: (12)..(12)
<223> OTHER INFORMATION: Leucine may be amidated

<400> SEQUENCE: 39

Ala Ser Xaa Leu Xaa Lys Leu Xaa Lys Xaa Leu Leu
1               5                   10

<210> SEQ ID NO 40
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
```

```
<222> LOCATION: (12)..(12)
<223> OTHER INFORMATION: Xaa is neurleucine
<220> FEATURE:
<221> NAME/KEY: misc_feature
<222> LOCATION: (12)..(12)
<223> OTHER INFORMATION: Neurleucine may be amidated

<400> SEQUENCE: 40

Ala Ser Xaa Leu Xaa Lys Leu Xaa Lys Arg Leu Xaa
1               5                   10

<210> SEQ ID NO 41
<211> LENGTH: 13
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (12)..(12)
<223> OTHER INFORMATION: Xaa is neurleucine
<220> FEATURE:
<221> NAME/KEY: misc_feature
<222> LOCATION: (13)..(13)
<223> OTHER INFORMATION: Neurleucine may be amidated
<220> FEATURE:
<221> NAME/KEY: misc_feature
<222> LOCATION: (13)..(13)
<223> OTHER INFORMATION: Xaa is neurleucine

<400> SEQUENCE: 41

Ala Ser Xaa Leu Xaa Lys Leu Xaa Lys Arg Leu Xaa Xaa
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (3)..(3)
<223> OTHER INFORMATION: Xaa is amino iso-butyric acid
<220> FEATURE:
<221> NAME/KEY: misc_feature
<222> LOCATION: (5)..(5)
<223> OTHER INFORMATION: Xaa is ornithine
<220> FEATURE:
<221> NAME/KEY: misc_feature
<222> LOCATION: (8)..(8)
<223> OTHER INFORMATION: Xaa is amino iso-butyric acid
<220> FEATURE:
<221> NAME/KEY: misc_feature
<222> LOCATION: (10)..(10)
<223> OTHER INFORMATION: Xaa is ornithine
```

```
<220> FEATURE:
<221> NAME/KEY: misc_feature
<222> LOCATION: (12)..(12)
<223> OTHER INFORMATION: Neurleucine may be amidated
<220> FEATURE:
<221> NAME/KEY: misc_feature
<222> LOCATION: (12)..(12)
<223> OTHER INFORMATION: Xaa is neurleucine

<400> SEQUENCE: 42

Ala Ser Xaa Leu Xaa Lys Leu Xaa Lys Xaa Leu Xaa
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:

```
<210> SEQ ID NO 45
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 45

Ala Ser His Cys Arg Lys Leu Cys Lys Arg Leu Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 46

Ala Ser Cys Leu Arg Lys Leu Cys Lys Arg Leu Leu
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Cysteine may be acetylated
<220> FEATURE:
<221> NAME/KEY: misc_feature
<222> LOCATION: (12)..(12)
<223> OTHER INFORMATION: Leucine may be amidated

<400> SEQUENCE: 47

Cys Ser His Leu Arg Lys Leu Cys Lys Arg Leu Leu
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 48
```

```
Ala Ser His Leu Arg Lys Cys Arg Lys Arg Cys Leu
1               5                   10
```

<210> SEQ ID NO 49
<211> LENGTH: 12
<212> TYPE: PRT
<213> ORGANISM: Artificial Sequence
<220> FEATURE:
<223> OTHER INFORMATION: Truncated analog of COG133
<220> FEATURE:
<221> NAME/KEY: misc_feature
<222> LOCATION: (1)..(1)
<223> OTHER INFORMATION: Alanine may be acetylated
<220> FEATURE:
<221> NAME/KEY: misc_feature
<222> LOCATION: (12)..(12)
<223> OTHER INFORMATION: Leucine may be amidated

<400> SEQUENCE: 49

```
Ala Ser His Cys Arg Lys Leu Arg Lys Arg Cys Leu
1               5                   10
```

<210> SEQ ID NO 50
<211> LENGTH: 13
<212> TYPE: PRT
<213> ORGANISM: Artificial Sequence
<220> FEATURE:
<223> OTHER INFORMATION: Protein transduction domain conjugate Tat

<400> SEQUENCE: 50

```
Gly Arg Lys Lys Arg Arg Gln Arg Arg Arg Pro Pro Gln
1               5                   10
```

<210> SEQ ID NO 51
<211> LENGTH: 16
<212> TYPE: PRT
<213> ORGANISM: Artificial Sequence
<220> FEATURE:
<223> OTHER INFORMATION: Protein transduction domain conjugate Antp

<400> SEQUENCE: 51

```
Arg Gln Ile Lys Ile Trp Phe Gln Asn Arg Arg Met Lys Trp Lys Lys
1               5                   10                  15
```

<210> SEQ ID NO 52
<211> LENGTH: 7
<212> TYPE: PRT
<213> ORGANISM: Artificial Sequence
<220> FEATURE:
<223> OTHER INFORMATION: Fragment of protein transduction domain
      conjugate Antp

<400> SEQUENCE: 52

```
Arg Arg Met Lys Trp Lys Lys
1               5
```

<210> SEQ ID NO 53
<211> LENGTH: 18
<212> TYPE: PRT
<213> ORGANISM: Artificial Sequence
<220> FEATURE:
<223> OTHER INFORMATION: Protein transduction domain conjugate

<400> SEQUENCE: 53

```
Arg Gly Gly Arg Leu Ser Tyr Ser Arg Arg Arg Phe Ser Thr Ser Thr
1               5                   10                  15

Gly Arg
```

```
<210> SEQ ID NO 54
<211> LENGTH: 10
<212> TYPE: PRT
<213> ORGANISM: Artificial Sequence
<220> FEATURE:
<223> OTHER INFORMATION: Protein transduction domain conjugate SynB3

<400> SEQUENCE: 54

Arg Arg Leu Ser Tyr Ser Arg Arg Arg Phe
1               5                   10

<210> SEQ ID NO 55
<211> LENGTH: 17
<212> TYPE: PRT
<213> ORGANISM: Artificial Sequence
<220> FEATURE:
<223> OTHER INFORMATION: Protein transduction domain conjugate SynB5

<400> SEQUENCE: 55

Arg Gly Gly Arg Leu Ala Tyr Leu Arg Arg Arg Trp Ala Val Leu Gly
1               5                   10                  15

Arg

<210> SEQ ID NO 56
<211> LENGTH: 8
<212> TYPE: PRT
<213> ORGANISM: Artificial Sequence
<220> FEATURE:
<223> OTHER INFORMATION: PolyArg

<400> SEQUENCE: 56

Arg Arg Arg Arg Arg Arg Arg Arg
1               5

<210> SEQ ID NO 57
<211> LENGTH: 60
<212> TYPE: PRT
<213> ORGANISM: Dendroaspis polylepis

<400> SEQUENCE: 57

Arg Ile Cys Tyr Ile His Lys Ala Ser Leu Pro Arg Ala Thr Lys Thr
1               5                   10                  15

Cys Val Glu Asn Thr Cys Tyr Lys Met Phe Ile Arg Thr Gln Arg Glu
                20                  25                  30

Tyr Ile Ser Glu Arg Gly Cys Gly Cys Pro Thr Ala Met Trp Pro Tyr
            35                  40                  45

Gln Thr Glu Cys Cys Lys Gly Asp Arg Cys Asn Lys
        50                  55                  60

<210> SEQ ID NO 58
<211> LENGTH: 60
<212> TYPE: PRT
<213> ORGANISM: Dendroaspis angusticeps

<400> SEQUENCE: 58

Trp Gln Pro Pro Trp Tyr Cys Lys Glu Pro Val Arg Ile Gly Ser Cys
1               5                   10                  15

Lys Lys Gln Phe Ser Ser Phe Tyr Phe Lys Trp Thr Ala Lys Lys Cys
                20                  25                  30
```

```
Leu Pro Phe Leu Phe Ser Gly Cys Gly Gly Asn Ala Asn Arg Phe Gln
        35                  40                  45

Thr Ile Gly Glu Cys Arg Lys Lys Cys Leu Gly Lys
    50                  55                  60
```

TREATMENT OF SUBARACHNOID HEMORRHAGE WITH APOE ANALOGS

CROSS-REFERENCE TO RELATED APPLICATIONS

This application is a continuation of U.S. patent application Ser. No. 12/023,288, filed Jan. 31, 2008, now U.S. Pat. No. 8,034,762, which is a continuation-in-part of U.S. application Ser. No. 11/661,777, filed Apr. 11, 2008, now U.S. Pat. No. 7,947,645, which is a national stage application of International Application No. PCT/US05/31431, filed Sep. 2, 2005, which in turn claims priority to U.S. Provisional Application Nos. 60/608,148, filed Sep. 9, 2004, 60/606,506, filed Sep. 2, 2004, and 60/606,507, filed Sep. 2, 2004, which are incorporated by reference in their entireties. U.S. patent application Ser. No. 12/023,288 also claims the benefit under 35 U.S.C. §119(e) of U.S. Provisional Application No. 60/898,392, filed Jan. 31, 2007, which is herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: COGO 015 02US SeqList_ST25.txt, date recorded: Oct. 20, 2011, file size 32 kilobytes).

FIELD OF THE INVENTION

The present invention provides the use of ApoE analogs in the treatment, prevention and amelioration of neurological signs and symptoms associated with cerebral vasospasm and various types of cerebral hemorrhages including subarachnoid hemorrhage, intracerebral hemorrhage, and intraventricular hemorrhage.

BACKGROUND

Stroke is a manifestation of vascular injury to the brain which is commonly secondary to arteriosclerosis or cardiac disease, and is the third leading cause of death (and the second most common cause of neurological disability) in the United States.

Stroke can be categorized into two major types, "ischemic stroke" and "hemorrhagic stroke." Ischemic stroke encompasses thrombotic, embolic, lacunar and hypo perfusion types of strokes. In contrast to ischemic stroke, hemorrhagic stroke is caused by intracerebral hemorrhage, subarachnoid hemorrhage, and intraventricular hemorrhage, i.e., bleeding into brain tissue, following blood vessel rupture within the brain.

Subarachnoid hemorrhage (SAH) is a condition in which blood collects beneath the arachnoid mater, a membrane that covers the brain. This area, called the subarachnoid space, normally contains cerebrospinal fluid. The accumulation of blood in the subarachnoid space can lead to stroke, seizures, and other complications. Additionally, subarachnoid hemorrhages may cause permanent brain damage and a number of harmful biochemical events in the brain. In some instances, subarachnoid hemorrhages include non-traumatic types of hemorrhages, usually caused by rupture of a berry aneurysm or arteriovenous malformation (AVM). Other causes include bleeding from a vascular anomaly and extension into the subarachnoid space from a primary intracerebral hemorrhage. Symptoms of subarachnoid hemorrhage include sudden and severe headache, nausea and/or vomiting, symptoms of meningeal irritation (e.g., neck stiffness, low back pain, bilateral leg pain) photophobia and visual changes, and/or loss of consciousness.

Subarachnoid hemorrhage is often secondary to a head injury or a blood vessel defect known as an aneurysm. In some instances, subarachnoid hemorrhage can induce a cerebral vasospasm that may in turn lead to an ischemic stroke. A common manifestation of a subarachnoid hemorrhage is the presence of blood in the CSF.

Subjects having a subarachnoid hemorrhage can be identified by a number of symptoms. For example, a subject having a subarachnoid hemorrhage will present with blood in the subarachnoid, usually in a large amount. Subjects having a subarachnoid hemorrhage can also be identified by an intracranial pressure that approximates mean arterial pressure, by a fall in cerebral perfusion pressure or by the sudden transient loss of consciousness (sometimes preceded by a painful headache). In about half of cases, subjects present with a severe headache which may be associated with physical exertion. Other symptoms associated with subarachnoid hemorrhage include nausea, vomiting, memory loss, hemiparesis and aphasia. Subjects having a subarachnoid hemorrhage can also be identified by the presence of creatine kinase-BB isoenzyme activity in their CSF. This enzyme is enriched in the brain but is normally not present in the CSF. Thus, its presence in the CSF is indicative of "leak" from the brain into the subarachnoid. Assay of creatine-kinase BB isoenzyme activity in the CSF is described by Coplin et al. (Coplin, et al, Arch Neurol, 1999, 56(11):1348-1352) Additionally, a spinal tap or lumbar puncture can be used to demonstrate if there is blood present in the CSF, a strong indication of a subarachnoid hemorrhage. A cranial CT scan or an MRI can also be used to identify blood in the subarachnoid region. Angiography can also be used to determine not only whether a hemorrhage has occurred but also the location of the hemorrhage.

Subarachnoid hemorrhage commonly results from rupture of an intracranial saccular aneurysm or from malformation of the arteriovenous system in, and leading to, the brain. Accordingly, a subject at risk of having a subarachnoid hemorrhage includes subjects having a saccular aneurysm as well as subjects having a malformation of the arteriovenous system. It is estimated that 5% of the population have such aneurysms yet only 1 in 10,000 people actually have a subarachnoid hemorrhage. The top of the basilar artery and the junction of the basilar artery with the superior cerebellar or the anterior inferior cerebellar artery are common sites of saccular aneurysms. Subjects having a subarachnoid hemorrhage may be identified by an eye examination, whereby slowed eye movement may indicate brain damage. A subject with a developing saccular aneurysm can be identified through routine medical imaging techniques, such as CT and MRI. A developing aneurysm forms a mushroom-like shape (sometimes referred to as "a dome with a neck" shape).

Among patients who suffer SAH and survive the initial ictus, vasospasm remains the most feared medical complication. A vasospasm is a sudden decrease in the internal diameter of a blood vessel that results from contraction of smooth muscle within the wall of the vessel. Vasospasms result in decreased blood flow, but increased system vascular resistance. It is generally believed that vasospasm is caused by local injury to vessels, such as that which results from atherosclerosis and other structural injury including traumatic head injury. Cerebral vasospasm is a naturally occurring vasoconstriction which can also be triggered by the presence of blood in the CSF, a common occurrence after rupture of an aneurysm or following traumatic head injury. Cerebral vasospasm can ultimately lead to brain cell damage, in the form of cerebral ischemia and infarction, due to interrupted blood supply. Cerebral vasospasm can occur any time after rupture of an aneurysm but most commonly peaks at seven days following the hemorrhage and often resolves within 14 days when the blood has been absorbed by the body.

A subject having a vasospasm is a subject who presents with diagnostic markers and symptoms associated with vasospasm. Diagnostic markers include the presence of blood in the CSF and/or a recent history of a subarachnoid hemorrhage. Vasospasm associated symptoms include paralysis on one side of the body, inability to vocalize the words or to understand spoken or written words, and inability to perform tasks requiring spatial analysis. Such symptoms may develop over a few days, or they may fluctuate in their appearance, or they may present abruptly.

MR angiography and CT angiography can be used to diagnose cerebral vasospasm. Angiography is a technique in which a contrast agent is introduced into the blood stream in order to view blood flow and/or arteries. A contrast agent is required because blood flow and/or arteries are sometimes only weakly apparent in a regular MR or CT scan. Appropriate contrast agents will vary depending upon the imaging technique used. For example, gadolinium is a common contrast agent used in MR scans. Other MR appropriate contrast agents are known in the art. Transcranial Doppler ultrasound can also be used to diagnose and monitor the progression of a vasospasm. As mentioned earlier, the presence of blood in the cerebrospinal fluid can be detected using CT scans. However, in some instances where the amount of blood is so small as to not be detected by CT, a lumbar puncture is warranted.

Vasospasm is a frequent source of secondary stroke and the delayed ischemic deficits that usually develop within the first 2 weeks after hemorrhage (Mendelow et al., 1988). At present, there are significant limitations to the treatment of aneurysmal SAH-induced cerebral vasospasm. Current therapeutic options include intracranial angioplasty, triple-H (hypervolemia, hemodilution, and hypertension) therapy, and oral administration of nimodipine as vasospasm prophylaxis. However, because the majority of patients who suffer SAH either die or become permanently disabled, there is substantial room for improvement in treatment strategies for this group of patients (Allen et al., 1983).

Nimodipine was introduced as a therapeutic agent for the prophylaxis of vasospasm based on findings of a small randomized clinical trial in the U.S. (Allen et al., 1983) and a large trial in the United Kingdom (Pickard et al. 1989). Both trials revealed modest improvements in neurological outcomes following nimodipine administration. Although the drug is accepted as the standard of care, the mechanism by which it works remains controversial. In addition to causing vascular relaxation, nimodipine may also serve as a neuroprotectant by blocking early neuronal calcium influx in the setting of acute ischemia (Inzitari et al., 2005; Korenkov et al., 2000). However, despite an improvement in functional outcome, no difference in angiographic vasospasm was observed between treatment and placebo in several trials (Allen et al., 1983; Petruck et al. 1988; Pickard et al. 1989). Thus, new drugs for the effective treatment and prevention of SAH and other cerebral hemorrhages are much desired.

SUMMARY

The present inventors have surprisingly found that ApoE analogs may be used as an effective therapy for SAH and other cerebral hemorrhages. The present invention is based, at least in part, on the discovery that administration of ApoE analogs for the treatment of cerebral hemorrhage is well tolerated, reduces hemorrhage growth, improves functional outcome, and decreases vasospasm and mortality. Accordingly, the present invention provides methods of using ApoE analogs described herein to treat, prevent or ameliorate cerebral hemorrhage, cerebral vasospasm, and disorders and the like.

In one embodiment, the present invention provides methods for treating, preventing or ameliorating subarachnoid hemorrhage (SAH). In another embodiment, the present invention provides methods for treating, preventing or ameliorating intracerebral hemorrhage (ICH). In yet another embodiment, the present invention provides methods for the treatment, prevention or amelioration of symptoms of intraventricular hemorrhage (IVH).

One aspect of the present invention provides methods of treating or ameliorating symptoms associated with cerebral hemorrhage by administering at least one ApoE analog. Suitable analogs for use in the present invention include those documented in PCT application No. PCT/US2005/31431, which is herein incorporated in its entirety. The at least one analog can be administered in an amount that reduces the symptoms of cerebral hemorrhage as compared to that which would occur in the absence of the analog. In certain embodiments, the methods of the invention reduce CNS trauma, CNS inflammation, cerebral ischemia or cerebral edema following SAH, IVH, and ICH. In certain embodiments, the methods hasten recovery from SAH, IVH, and ICH. In certain embodiments, the methods improve functional recovery or cognitive function following SAH, IVH, and ICH.

The invention also provides the use of ApoE analogs for preventing or attenuating hemorrhage growth, following intraventricular hemorrhage (IVH), intracerebral hemorrhage (ICH), and/or subarachnoid hemorrhage (SAH). Typical human subjects for whom the treatment is intended are those suffering from coagulopathic bleedings, including, without limitation, human subjects who have experienced aneurismal subarachnoid hemorrhage.

In one embodiment, the ApoE analog is a naturally occurring or synthetic ApoE polypeptide or a biologically active fragment thereof. In another embodiment, the ApoE analog is a nucleic acid encoding ApoE or a biologically active fragment thereof. In still another embodiment, the ApoE analog is an agonist of ApoE. Suitable analogs for use in the present invention include those documented in PCT application No. PCT/US2005/31431, which is herein incorporated in its entirety. In certain embodiments, the ApoE analogs are polypeptides comprising a sequence of SEQ ID Nos 1-56.

In certain embodiments, the invention provides pharmaceutical compositions comprising at least one of the ApoE analogs described herein. In certain embodiments, the invention provides pharmaceutical compositions comprising at least one ApoE analog described herein with another active agent for the treatment, prevention or amelioration of cerebral hemorrhage or cerebral vasospasm. The pharmaceutical compositions of the invention can be provided in such a way as to facilitate administration to a subject in need thereof, including, for example, by intravenous, intramuscular, subcutaneous or transdermal administration. See, Remingtons Pharmaceutical Sciences, 19th ed. Remington and Gennaro, eds. Mack Publishing Co., Easton, Pa., incorporated herein by reference. The methods of the present invention further provide for various dosing schedules, administration times, intervals and duration to treat, prevent or ameliorate the disorders described herein. Also included are functional variants of the disclosed compounds and variants identified using the assays disclosed in the present invention, wherein such compounds mediate the functional effects disclosed herein. Consistent therewith, the invention also includes use of the disclosed compounds and functional variants thereof in methods of making medicaments for treating the various diseases and disorders discussed herein.

The invention also provides the use of ApoE analog for increasing the overall survival of a subject following the start of treatment.

In another embodiment, the ApoE analog is administered in conjunction with another active agent. The active agent may be a voltage-gated calcium channel inhibitor, i.e., nimodipine.

In one aspect, the ApoE analog is first administered between about 12-24 hours after diagnosis of intraventricular hemorrhage, intracerebral hemorrhage, and/or subarachnoid hemorrhage. In another embodiment the ApoE analog is first administered between about 24-72 hours after diagnosis of intraventricular hemorrhage, intracerebral hemorrhage, and/or subarachnoid hemorrhage.

In one embodiment, the ApoE analog is administered at least about every 4 hours. In another embodiment, the ApoE analog is administered at least about every 5, 6, 7, 8, 9, 10, 11, or 12 hours.

In another embodiment, the methods of the invention use ApoE analogs which are administered in low doses ranging from 0.1 mg/kg-0.9 mg/kg. In another embodiment, the ApoE analog is administered in higher doses ranging from 1.0 mg/kg-1.9 mg/kg.

In one embodiment, the present invention provides methods of administering the ApoE analogs during or contemporaneously with a cerebral hemorrhage surgery.

Figure 1:
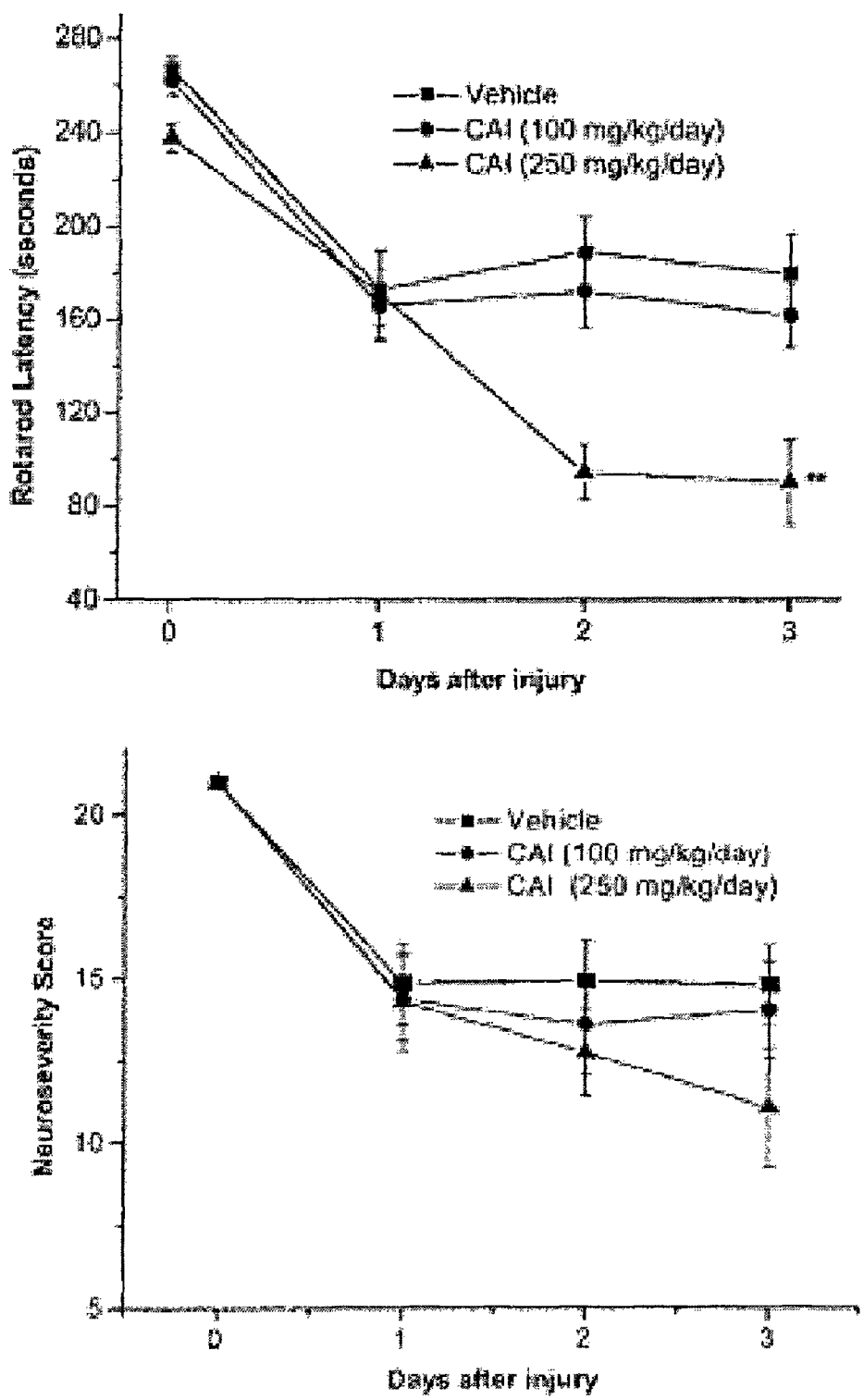
FIG. 1 is a line graph demonstrating the effects of carboxyamidotriazole (CAI) on rotarod latency and neurological severity scores. Administration of CAI at a dose of 250 mg/kg/day results in significantly worse functional performance on the rotarod (upper) and a lower average neurological severity score (lower) than found in the vehicle-treated group. In the latter case, however, this difference did not reach statistical significance. **$p<0.001$.

Other features and advantages of the invention will be apparent from the following detailed description and claims.

DETAILED DESCRIPTION OF THE INVENTION

Methods

The present methods and ApoE analogs are useful in preventing, treating, or ameliorating neurological signs and symptoms associated with cerebral hemorrhage. As used herein, cerebral hemorrhages include, but are not limited to, intracerebral hemorrhage (ICH), subarachnoid hemorrhage (SAH), and intraventricular hemorrhage (IVH). The finding by the present inventors that ApoE analogs can be used to improve functional outcome, and decrease vasospasm and mortality following cerebral hemorrhage provides a role for the ApoE and ApoE analogs of the invention in the treatment of any symptoms associated with cerebral hemorrhage.

The present methods and compounds are also particularly useful in preventing, treating, or ameliorating the neurological signs and symptoms associated with cerebral vasospasm. As used herein, cerebral vasospasm refers to the delayed occurrence of narrowing of large capacity arteries at the base of the brain after subarachnoid hemorrhage, often associated with diminished perfusion in the territory distal to the affected vessel. In this regard, the ApoE analogs and other compounds of the invention can be used alone or in combination with other known anti-spasm drugs for the treatment of cerebral vasospasm associated with SAH, IVH, and ICH.

In one embodiment, the ApoE analog may be an ApoE peptide or ApoE mimetic peptide. Preferred ApoE mimetic peptides include COG133, a peptide of the sequence LRVR-LASHLRKLRKRLL (SEQ. ID. NO. 1), and derivatives of COG133 such as Ac-AS-Aib-LRKL-Aib-KRLL-amide (SEQ. ID. NO. 7; ApoE 1410) and other peptide mimetics as described herein.

As used herein, the terms "treating" and "ameliorating" are not necessarily meant to indicate a reversal or cessation of the disease process underlying the cerebral hemorrhage condition afflicting the subject being treated. Such terms indicate that the deleterious signs and/or symptoms associated with the condition being treated are lessened or reduced, or the rate of progression is reduced, compared to that which would occur in the absence of treatment. A change in a disease sign or symptom can be assessed at the level of the subject (e.g., the function or condition of the subject is assessed), or at a tissue or cellular level (e.g., the production of markers of glial or macrophage activation is lessened or reduced).

The invention also provides methods for reducing the risk of death in a SAH, ICH, and IVH subject, which are carried out by administering an amount of ApoE analog to the subject for preventing or attenuating vasospasm following SAH, ICH, and IVH.

The invention also provides methods for preventing or attenuating one or more complications of SAH, ICH, or IVH in a subject, which are carried out by: (i) administering to a SAH, ICH, or IVH subject an amount effective for achieving the prevention or attenuation of ApoE analogs; and (ii) observing a reduction in the frequency of occurrence of one or more complications of SAH, ICH, or IVH in the subject who received said ApoE analogs relative to the frequency of occurrence of said complications that would have been expected in the same subject who had not received said ApoE analogs.

The present invention provides methods and compositions that can be used advantageously to prevent or attenuate hemorrhage growth following SAH, ICH, and IVH, which a subject may experience subsequent to their injury and/or as a result of medical interventions that may be used to treat their injuries. The methods are carried out by administering to an SAH, ICH, and IVH subject, at least one ApoE analog, in a manner that is effective for preventing or attenuating hemorrhage growth, or any of these complications related to SAH, ICH, and IVH. Non-limiting examples of complications include: cerebral edema and poor neurological outcome after SAH, IVH, and ICH, and death. In some embodiments, the subject is suffering from spontaneous SAH, IVH, and ICH. In some embodiments, the subject is suffering from traumatic SAH, IVH, and ICH. A method effective for preventing or attenuating hemorrhage growth, or other subsequent complications may comprise administering a predetermined amount of ApoE or an ApoE analog, and/or utilizing a particular dosage regimen, formulation, mode of administration, combination with other treatments, and the like. The efficacy of the methods of the invention in reducing hemorrhage growth, or in preventing complications of SAH, IVH, and ICH may be assessed using one or more conventional imaging methods (e.g., CT, MRI scanning) or by use of parameters that evaluate complications.

Subjects who may benefit by use of the methods of the present invention include, without limitation, subjects who have suffered from spontaneous or traumatic SAH, IVH, and ICH. Spontaneous SAH, IVH, and ICH include subjects suffering an intracerebral bleed usually associated with the occurrence of advanced age, hypertension, or deposition of amyloid in the cerebral vasculature. SAH, IVH, and ICH usually results from the rupture of a single vessel causing extensive damage to the surrounding brain tissue adjacent to the damaged vessel. Traumatic SAH, IVH, and ICH may be associated with accidents resulting from e.g. motor vehicle accidents or fall from a height. The resulting contusion to the head may lead to the rupture of one or more intracerebral or extracerebral (but intracranial) vessels. Many intracranial (but extracerebral) bleedings are evacuated surgically already in the acute phase, whereas the intracerebral lesions more often are inaccessible to direct evacuation as the evacuation itself would cause significant damage to the brain tissue.

The methods of the present invention can be applied advantageously to any subject who has suffered spontaneous or traumatic SAH, IVH, and ICH that, if left untreated, would result in a significant growth of the hemorrhage and in associated complications.

The methods of the invention are also useful for treating extravascular hematomas and blood clots in a human subject. As used herein, the term "extravascular" includes a hematoma or blood clot that is found outside the vasculature, e.g., in the intraventricular or arachnoid space in the brain. The instant methods are directed to the use of a therapeutically effect amount of an ApoE analog. As used herein the term "therapeutically effective amount" of an ApoE analog includes an amount sufficient to provide a therapeutic benefit to a subject in need thereof. Therapeutic benefit may be determined by any of the methods described herein, and include, but are not limited to, decrease in blood clot size or volume, decrease in ICP, improvement in GCS, improvement in neurological function, and a decrease in predicted mortality. A therapeutically effective amount of an ApoE analog includes the parameters of both dosage amount (e.g., amount of ApoE analog administered at one time) and dosage interval (e.g., how often the ApoE analog is administered. In a most preferred embodiment, a therapeutically effective amount of a ApoE analog is an amount sufficient to reduce the blood clot to about 80% of its original size.

In another aspect, the invention encompasses the use of ApoE analogs for reducing the number of days a SAH, IVH, and ICH subject is hospitalized following symptom onset or injury onset. In some embodiments, the ApoE analog is for reducing the number of days a SAH, IVH, and ICH subject spends in an Intensive Care Unit (ICU) following injury or symptom onset.

In another aspect, the invention provides methods for reducing the number of days an ICH subject is hospitalized following spontaneous SAH, IVH, and ICH or traumatic SAH, IVH, and ICH, which are carried out by administering to the subject an effective amount for the reduction of at least one ApoE analog.

In another aspect, the invention provides kits or parts thereof for preventing or attenuating hemorrhage growth, following SAH, ICH, and IVH as well as preventing or attenuating one or more complications of SAH, ICH, and IVH, comprising (i) at least one ApoE analog (ii) Instructions for Use. The instructions may describe, for instance, that a first dose containing an effective amount of at least one ApoE analog is administered at the start of the treatment. A second dose may be needed and the ApoE analog should be administered one hour, two hours, three hours, four hours, five hours, etc. after the start of treatment.

In another aspect, the invention provides methods for improving brain function in a SAH, IVH, and ICH subject, which are carried out by administering to the subject an effective amount for the improving of at least one ApoE analog.

In another aspect, the invention provides methods for reducing the risk of developing complications of brain dysfunction including, but not limited to brain herniation, brain infarction in an SAH, IVH, and ICH subject, which methods are carried out by administering to the subject an effective amount for the reducing of at least one ApoE analog. In some embodiments, the invention provides methods for reducing the risk of progression from brain injury to brain death.

In another aspect, the invention provides methods for reducing the risk of death in a SAH, IVH, and ICH subject, which are carried out by administering to the subject an effective amount for the reducing of at least one ApoE analog.

In another aspect, the invention provides methods for preventing or attenuating hemorrhage growth, and/or edema generation following SAH, IVH, and ICH in a majority of spontaneous SAH, IVH, and ICH or traumatic SAH, IVH, and ICH subjects, which are carried out by (i) administering to a group of SAH, IVH, and ICH subjects an effective amount for the preventing or attenuating of at least one ApoE analog; and (ii) observing a reduction in the frequency of occurrence of one or more complications of SAH, IVH, and ICH among the group of subjects relative to the frequency of occurrence of the complications that would have been expected in the same group of human subjects who had not received the at least one ApoE analog.

ApoE Analogs

The present invention provides methods of treating, preventing, and ameliorating cerebral hemorrhage with ApoE analogs and derivatives. A large number of analogs of the apoE 130-150 peptide were previously created and their activity tested in a cell-based assay for suppression of release of inflammatory cytokines and free radicals and in receptor binding assays. Lynch et al., 2003, *J. Biol. Chem.* 278(4), 48529-33 and U.S. application Ser. No. 10/252,120 (filed Sep. 23, 2002), Ser. No. 09/957,909 (filed Sep. 21, 2001) and Ser. No. 09/260,430 (filed Mar. 1, 1999), now abandoned, which claims the benefit of U.S. Provisional Application No. 60/077,551 (filed Mar. 11, 1998), the contents of each of which are incorporated herein by reference in their entireties.

In one embodiment, the method of the present invention employs analogs and derivatives of COG133, a truncated peptide comprised of residues 133-149 of apoE. This truncated apoE peptide, referred to as COG133 (LRVRLASHL-RKLRKRLL (SEQ. ID. NO.1)) proved useful in treating or reducing cerebral ischemia or cerebral inflammation. U.S. application Ser. No. 10/252,120, filed Sep. 23, 2002, incorporated herein by reference in its entirety.

In practicing the present invention, any ApoE analogs may be used that are effective in preventing complications when administered to a SAH, ICH, and IVH human subject. Some of the ApoE analogs are described in U.S. application Ser. No. 10/252,120, filed Sep. 23, 2002 and PCT/US2005/031431, which are incorporated herein by reference in their entities.

ApoE analogs include, without limitation, naturally occurring or synthetic ApoE polypeptides or biologically active fragments thereof, nucleic acids encoding ApoE or biologically active fragments thereof and agonists of ApoE. The ApoE polypeptides may have either been chemically modified relative to human ApoE and/or contain one or more amino acid sequence alterations relative to human ApoE. Such ApoE peptides may exhibit different properties relative to human ApoE, including stability, phospholipid binding, altered specific activity, and the like.

Examples of ApoE peptide memetics include, without limitation,

LRVRLASHLRKLRKRLL (SEQ. ID. NO. 1)

LRVRLASH-(NMe)-L-RKLRKRLL-NH₂ (SEQ. ID. NO. 2)

Ac-ASH-Aib-RKLRKRLL-NH₂ (SEQ. ID. NO. 3)

Ac-AS-Aib-LRKLRKRLL-NH₂ (SEQ. ID. NO. 4)

Ac-DS-Aib-LRKLRKRLL-NH₂ (SEQ. ID. NO. 5)

Ac-ASHLRKL-Aib-KRLL-NH₂ (SEQ. ID. NO. 6)

Ac-AS-Aib-LRKL-Aib-KRLL-NH₂ (SEQ. ID. NO. 7)

Ac-DR-Aib-ASHLRKLRKR-Aib-L-NH₂ (SEQ. ID. NO. 8)

Ac-DS-Aib-LRKLRKR-Aib-L-NH₂ (SEQ. ID. NO. 9)

Ac-DR-Aib-ASHLRKL-Aib-KRLL-NH₂ (SEQ. ID. NO. 10)

Ac-DS-Aib-LRKL-Aib-KRLL-NH₂ (SEQ. ID. NO. 11)

Ac-DR-Aib-AS-Aib-LRKLRKRLL-NH₂ (SEQ. ID. NO. 12)

Ac-DR-Aib-ASHLRKLRKRLL-NH₂ (SEQ. ID. NO. 13)

Ac-CAS-Aib-LRKL-Aib-KRLL-NH₂ (SEQ. ID. NO. 14)

Ac-DS-Aib-LRKL-Aib-KRLL-NH₂ (SEQ. ID. NO. 15)

Ac-AS-Aib-LRKL-Aib-KRLV-NH₂ (SEQ. ID. NO. 16)

Ac-AS-Aib-LRKL-Aib-KRLM-NH₂ (SEQ. ID. NO. 17)

Ac-AS-Aib-LRKL-Aib-KRLI-NH₂ (SEQ. ID. NO. 18)

Ac-AS-Aib-LRKL-Aib-KRLA-NH₂ (SEQ. ID. NO. 19)

Ac-AS-Aib-LRKL-Aib-KALL-NH₂ (SEQ. ID. NO. 20)

Ac-AS-Aib-LRKL-Aib-K(orn)LL-NH₂ (SEQ. ID. NO. 21)

Ac-AS-Aib-LRKL-Aib-K(narg)LL-NH₂ (SEQ. ID. NO. 22)

Ac-AS-Aib-LRKL-Aib-K(harg)LL-NH₂ (SEQ. ID. NO. 23)

Ac-AS-Aib-LRKL-Aib-K(dmarg)LL-NH₂ (SEQ. ID. NO. 24)

Ac-AS-Aib-LRKL-Aib-ARLL-NH₂ (SEQ. ID. NO. 25)

Ac-AS-Aib-LRKL-Aib-(aclys)RLL-NH₂ (SEQ. ID. NO. 26)

Ac-AS-Aib-LRKL-Aib-(azlys)RLL-NH₂ (SEQ. ID. NO. 27)

Ac-ASH-Aib-RKL-Aib-KRLL-NH₂ (SEQ. ID. NO. 28)

Ac-AS-Aib-LRKL-Aib-KRL-(NLe)-NH₂ (SEQ. ID. NO. 29)

Ac-AS-Aib-LRKL-Aib-KR-(NLe)-L-NH₂ (SEQ. ID. NO. 30)

-continued

Ac-AS-Aib-LRKL-Aib-KR-(NLe)-(Nle)-NH₂ (SEQ. ID. NO. 31)

Ac-AS-Aib-LRKL-Aib-K(orn)L-(NLe)-NH₂ (SEQ. ID. NO. 32)

Ac-AS-Aib-LRKL-Aib-K(orn)-(NLe)-L-NH₂ (SEQ. ID. NO. 33)

Ac-AS-Aib-LRKL-Aib-K(orn)-(NLe)-(Nle)-NH₂ (SEQ. ID. NO. 34)

Ac-AS-Aib-LRKL-Aib-K(harg)L-(NLe)-NH₂ (SEQ. ID. NO. 35)

Ac-AS-Aib-LRKL-Aib-K(harg)-(NLe)-L-NH₂ (SEQ. ID. NO. 36)

Ac-AS-Aib-LRKL-Aib-K(harg)-(NLe)-(Nle)-NH₂ (SEQ. ID. NO. 37)

Ac-AS-Aib-L(orn)KL-Aib-KRLL-NH₂ (SEQ. ID. NO. 38)

Ac-AS-Aib-L(orn)KL-Aib-K(orn)LL-NH₂ (SEQ. ID. NO. 39)

Ac-AS-Aib-L(orn)KL-Aib-KRL-(NLe)-NH₂ (SEQ. ID. NO. 40)

Ac-AS-Aib-L(orn)KL-Aib-KRL-(NLe)-(Nle)-NH₂ (SEQ. ID. NO. 41)

Ac-AS-Aib-L(orn)KL-Aib-K(orn)L-(Nle)-NH₂ (SEQ. ID. NO. 42)

Ac-AS-Aib-L(orn)KL-Aib-K(orn)-(NLe)-(Nle)-NH₂ (SEQ. ID. NO. 43)

Ac-ASHLRKLRKRLL-NH₂ (apoe138-149) (SEQ. ID. NO. 44)

Ac-ASHCRKLCKRLL-NH₂ (SEQ. ID. NO. 45)

Ac-ASCLRKLCKRLL-NH₂ (SEQ. ID. NO. 46)

Ac-CSHLRKLCKRLL-NH₂ (SEQ. ID. NO. 47)

Ac-ASHLRKCRKRCL-NH₂ (SEQ. ID. NO. 48)

Ac-ASHCRKLRKRCL-NH₂ (SEQ. ID. NO. 49)

wherein (NMe)-L is an N-methylated Leucine, Aib is amino iso-butyric acid, (orn) is ornithine, (narg) is nitroarginine, (NLe) is neurleucine, (harg) is homoarginine, (dmarg) is dimethyl arginine, (aclys) is acetyl lysine, (azlys) is azalysine and Ac is an acetylated amino terminus. The one letter abbreviation for the amino acid residues are well known to those skilled in the art.

In one aspect, the compounds are analogs or peptide mimetics of an ApoE protein. In yet another preferred embodiment, the peptide is AcASHLRKLAibKRLL (SEQ. ID. NO. 6) (COG432). In another preferred embodiment, the peptide is Ac-AS-Aib-LRKL-Aib-KRLL-NH₂ (SEQ. ID. NO. 7) (ApoE-1410). In certain embodiments, the present invention provides peptide mimetics that mimic the functionality of the active peptide and methods of making the same, as described in detail hereinbelow.

The present invention provides protein transduction domains (PTD) conjugated to an ApoE analog. PTDs are heterogeneous in size and lack sequence homology, although most share a positive charge and are amphipathic.

In treating CNS disorders and injuries, the blood brain barrier (BBB) drastically limits the transport of polar molecules, such as peptides, into the brain. Preliminary data in vivo indicate that the efficacy of ApoE peptide mimetics can be significantly improved by conjugation to a protein transduction domain (PTD). PTDs are short basic peptides that promote the intracellular delivery of cargo that would otherwise fail to, or only minimally, traverse the cell membrane.

However, the ability of a PTD to transport cargo intracellularly does not guarantee it is capable of transport through the BBB, which is significantly more complex of a process, and the number of PTDs tested for the transport of cargo across the BBB in vivo has been relatively few. Therefore, the appropriate PTD for BBB transport needs to be determined empirically, and/or created by modifications of known PTDs. The present invention provides compounds comprising PTD conjugations of apoE analogs and derivatives, including ApoE and derivatives and analogs thereof.

Without being bound to any theory, it is hypothesized that PTDs can enhance CNS penetration of compounds, including apoE analog peptides. By increasing CNS penetration, the PTD-apoE analog conjugated compounds described herein can increase the efficacy of the apoE analogs and extend the therapeutic window, i.e., length of time between brain injury and efficacious administration of the apoE analogs, including COG133. Preliminary data indicate that COG133 was neuroprotective when administered up to 30 minutes post TBI, whereas a PTD-COG133 conjugate was equally effective when administered up to 150 minutes following TBI. This represents a substantial increase in the therapeutic window that could dramatically expand the number of human subjects that can be helped by this novel therapeutic compound. Furthermore, enhancing the BBB penetrability of the apoE analogs, including COG133, can render these compounds useful for the treatment, prevention or amelioration of numerous inflammation-based neurodegenerative diseases, regardless of whether the BBB is compromised.

The PTD conjugates of the invention also provide the added benefit of lowering the amount of drug (COG133) needed to be administered because of specific targeting to the brain. This provides a better therapeutic index for the conjugated compounds, which is the maximum tolerated dose of compound when no death is seen, divided by the minimum effective dose of compound needed to be given to see the desired protective effect. The greater the index, the safer a compound should be because the side effect profile should be decreased at the concentration needed to see the desired protective effect. Different PTD's could be made to preferentially target other specific tissues and/or organs depending on the disorder to be treated.

The PTDs of the present invention are those that facilitate CNS penetration or facilitate intracellular transport. In certain embodiments, PTDs can be antimicrobial peptides such as protegrin 1, Bactenecin 7, Buforin, and Maginin; a host of arginine-rich RNA- and DNA-binding peptides (e.g., HIV-1 transactivating protein (TAT) and *Drosophila* homeodomain transcription factor Antennapedia (a.k.a. Penetratin); chimeric PTDs such as Transportan; lysine- and arginine-rich peptides derived from phage-display libraries; polyarginine; and most recently, β-homolysine oligomers (See, Fisher et al., 2001; Lindsay, 2002; Tung et al., 2003; Leifert et al., 2003; Bogoyevitch et al., 2002; Garcia-Echeverria 2003, incorporated herein by reference in their entireties). In certain embodiments, the PTDs are addition, reverso-, retro-inverso, and enantio-forms of many of the PTDs described herein.

In a preferred embodiment, the present invention provides PTD conjugates selected from the group consisting of:

```
GRKKRRQRRRPPQ        (SEQ. ID. NO. 50)

RQIKIWFQNRRMKWKK     (SEQ. ID. NO. 51)

RRMKWKK              (SEQ. ID. NO. 52)

RGGRLSYSRRRFSTSTGR   (SEQ. ID. NO. 53)

RRLSYSRRRF           (SEQ. ID. NO. 54)

RGGRLAYLRRRWAVLGR    (SEQ. ID. NO. 55)

RRRRRRRR             (SEQ. ID. NO. 56)
```

In certain embodiments, the PTD conjugate is RGGRLAYLRRRWAVLGR (SEQ. ID. NO. 55), referred to as SynB5, or RRLSYSRRRF (SEQ ID NO. 54) referred to as SynB3. PTD-apoE conjugate compounds of the invention include, for instance, SynB5-COG133, SynB3-COG133, or Syn B5 and Syn B3 conjugates of any of the COG133 analogs described herein.

Accordingly, PTD transport was initially characterized as receptor- and energy-independent, nonendocytic, and lacking in cell specificity. However, these data were collected through analysis of cellular uptake via fluorescence microscopy on fixed cells or flow cytometry. Several groups have recently demonstrated that data collected in this manner was subject to an artifact of cell fixation (Futaki, 2002; Vives et al., 2003; Suzuki, 2001; Richard et al., 2003; Lundberg et al., 2002; Thoren, et al., 2003, incorporated herein by reference in their entireties). It is becoming clear that a number of these PTDs, e.g., penetratin TAT, poly-arginine; are taken up via endocytosis (Drin et al., 2003; Thoren et al., 2003, incorporated herein by reference in their entireties). The same methodology was also used for analysis of structure-activity relationships of PTDs. The validity of the results of these studies, as well as studies of cell specificity, which were also derived from fixed cells, is therefore called into question. For example, the uptake of penetratin in living cells was recently demonstrated to be endocytic. Furthermore, substitution of two tryptophan residues, previously identified as critical for transcytosis, did not modify the uptake of penetratin (Thoren et al., 2003, incorporated herein by reference in its entirety).

Questions regarding mechanism of transport aside, there are numerous reports of the biological effects of cargo carried by PTDs, including peptides, proteins, peptide nucleic acids, oligonucleotides, liposomes, and magnetic nanoparticles, substantiating their capability for translocation (Schwarze et al, 2000; Bogoyevitch et al., 2002; Tung et al., 2003; Vives et al., 2003, incorporated herein by reference in their entireties). It is becoming clear that our knowledge regarding PTDs needs to be re-evaluated, and that transport mechanisms likely vary among the PTDs, perhaps as their primary structures also vary.

Comparative studies indicated that PTDs are not interchangeable; they differ in uptake rate, concentration required for translocation, toxicity, and cellular context (Thoren et al., 2003; Suzuki et al., 2002; Mai, et al., 2002, incorporated herein by reference in their entireties). Studies using live cells have reported that a PTD can have multiple modes of transport which can differ according to cellular context (Drin et al., 2003; Futaki, 2002; Leifert et al., 2003, incorporated herein by reference in their entireties). Recent data indicate that PTDs exhibit cell specificity, the source of which can be preferential interaction of PTDs with specific cell surface glycosaminoglycans (Mai et al., 2002; Console et al., 2003; Koppelhus et al., 2002, incorporated herein by reference in their entireties). Evidence to this effect comes from studies that show dextran sulfate inhibited uptake of TAT, but not penetratin complexes, and heparin inhibited internalization of TAT and penetratin complexes to different degrees (Console et al., 2003, incorporated herein by reference in their entireties). These data suggest selectively targeting tissues may be possible by optimizing the PTD to target specific cell surface-expressed glycosaminoglycans. Clearly, there is no PTD that is optimal for cargo delivery across the board. PTD, cargo, and target organ all must be taken into account.

Compound Preparation

Peptides of the present invention can be produced by standard techniques as are known in the art as well as what has been described in U.S. application Ser. No. 10/252,120, filed Sep. 23, 2002 and PCT US2005/031431, which are incorporated herein by reference in their entities.

Modification of the peptides disclosed herein to enhance the functional activities associated with these peptides could be readily accomplished by those of skill in the art. For instance, the peptides used in the methods of the present invention can be chemically modified or conjugated to other molecules in order to enhance parameters like solubility, serum stability, etc, while retaining functional activity. In particular, the peptides of the invention may be acetylated at the N-terminus and/or amidated at the C-terminus, or conjugated, complexed or fused to molecules that enhance serum stability, including but not limited to albumin, immunoglobulins and fragments thereof, transferrin, lipoproteins, liposomes, α-2-macroglobulin and α-1-glycoprotein, PEG and dextran. Such molecules are described in detail in U.S. Pat. No. 6,762,169, which is herein incorporated by reference in its entirety.

Small molecules that target the conjugate to specific cells or tissues may also be used. It is known that presence of a biotin-avidin complex increases uptake of such modified peptides across endothelial cells. Linkage of peptides to carbohydrate moieties, for example to a β-glycoside through a serine residue on the peptide to form a β-O linked glycoside, enhances transport of the glycoside derivative via glucose transporters (Polt, R. et al. Proc. Natl. Acad. Sci. USA 91:7144-7118 (1994); Oh et al. Drug Transport and targeting, In Membrane Transporters as Drug Targets, Amidon, G. L. and Sadee, W. eds., pg 59-88, Plenum Press, New York, 1999).

The peptides may have attached various label moieties such as radioactive labels and fluorescent labels for detection and tracing. Fluorescent labels include, but are not limited to, fluorescein, eosin, Alexa Fluor, Oregon Green, rhodamine Green, tetramethylrhodamine, rhodamine Red, Texas Red, coumarin and NBD fluorophores, the QSY 7, dabcyl and dabsyl chromophores, BODIPY, Cy5, etc.

In another aspect, other naturally occurring or synthetic peptides and proteins may be used to provide a carrier immunogen for generating antibodies to the subject peptides, where the antibodies serve as reagents for detecting the immunomodulatory peptides or for identifying other peptides having a comparable conformation. Suitable carriers for generating antibodies include, among others, hemocyanins (e.g., Keyhole Limpet hemocyanin—KLH); albumins (e.g., bovine serum albumin, ovalbumin, human serum albumin, etc.); immunoglobulins; thyroglobulins (e.g., bovine thyroglobulin); toxins (e.g., diptheria toxoid, tetanus toxoid); and polypeptides such as polylysine or polyalanine-lysine. Although proteins are preferred carriers, other carriers, preferably high molecular weight compounds, may be used, including carbohydrates, polysaccharides, lipopolysaccharides, nucleic acids, and the like of sufficient size and immunogenicity. In addition, the resulting antibodies may be used to prepare anti-idiotypic antibodies which may compete with the subject peptides for binding to a target site. These anti-idiotypic antibodies are useful for identifying proteins to which the subject peptides bind.

Another variation of the therapeutic peptides of the present invention is the linking of from one to fifteen amino acids or analogs to the N-terminal or C-terminal amino acid of the therapeutic peptide. Analogs of the peptides of the present invention can also be prepared by adding from one to fifteen additional amino acids to the N-terminal, C-terminal, or both N- and C-terminals, of an active peptide, where such amino acid additions do not adversely affect the ability of the peptide to bind to receptors at the site bound by a peptides of the invention.

The peptides of the present invention further include conservative variants of the peptides herein described. As used herein, a conservative variant refers to alterations in the amino acid sequence that do not adversely affect the biological functions of the peptide. A substitution, insertion or deletion is said to adversely affect the peptide when the altered sequence prevents or disrupts a biological function associated with the peptide. For example, the overall charge, structure or hydrophobic/hydrophilic properties of the peptide may be altered without adversely affecting a biological activity. Accordingly, the amino acid sequence can be altered, for example to render the peptide more hydrophobic or hydrophilic, without adversely affecting the biological activities of the peptide.

Ordinarily, the conservative substitution variants, analogs, and derivatives of the peptides, will have an amino acid sequence identity to the disclosed sequences SEQ ID NOs: 1-56 of at least about 55%, at least about 65%, at least about 75%, at least about 80%, at least about 85%, at least about 90%, at least about 95%, or at least about 96% to 99%. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

Thus, the peptides of the present invention include molecules having the amino acid sequence disclosed in SEQ ID Nos. 1-56; fragments thereof having a consecutive sequence of at least about 3, 4, 5, 6, 10, 15, or more amino acid residues of the therapeutic peptide; amino acid sequence variants of such peptides wherein an amino acid residue has been inserted N- or C-terminal to, or within, the disclosed sequence; and amino acid sequence variants of the disclosed sequence, or their fragments as defined above, that have been substituted by another residue. Peptide compounds comprising the peptide sequences of the invention may be 15, 20, 25, 30, 35, 40, 45, 50 or more amino acids. Contemplated variants further include those containing predetermined mutations by, e.g., homologous recombination, site-directed or PCR mutagenesis, and the corresponding peptides of other animal species, including but not limited to rabbit, rat, porcine, bovine, ovine, equine and non-human primate species, and derivatives wherein the peptide has been covalently modified by substitution, chemical, enzymatic, or other appropriate means with a moiety other than a naturally occurring amino acid (for example a detectable moiety such as an enzyme or radioisotope).

Therapeutic peptides of the present invention can be in free form or the form of a salt, where the salt is pharmaceutically acceptable. These include inorganic salts of sodium, potassium, lithium, ammonium, calcium, magnesium, iron, zinc, copper, manganese, and the like. Various organic salts of the peptide may also be made with, including, but not limited to, acetic acid, propionic acid, pyruvic acid, maleic acid, succinic acid, tartaric acid, citric acid, benozic acid, cinnamic acid, salicylic acid, etc.

Compositions

Compounds and therapeutic peptides of the present invention can be in free form or the form of a salt, where the salt is pharmaceutically acceptable.

As used herein, the term "administering to the brain of a subject" refers to the use of routes of administration, as are known in the art, that provide the compound to the central nervous system tissues, and in particular the brain, of a subject being treated.

Preferably, the compounds of the present invention are used in combination with a pharmaceutically acceptable carrier. The present invention thus also provides pharmaceutical compositions suitable for administration to a subject. Such compositions comprise an effective amount of the compound of the present invention in combination with a pharmaceutically acceptable carrier. The carrier can be a liquid, so that the composition is adapted for parenteral administration, or can be solid, i.e., a tablet or pill formulated for oral administration. Further, the carrier can be in the form of a nebulizable liquid or solid so that the composition is adapted for inhalation. When administered parenterally, the composition should be pyrogen free and in an acceptable parenteral carrier. Active compounds can alternatively be formulated encapsulated in liposomes, using known methods. Additionally, the intranasal administration of peptides to treat CNS conditions is known in the art (see, e.g., U.S. Pat. No. 5,567,682, incorporated herein by reference to Pert, regarding intranasal administration of peptide T to treat AD). Preparation of a Compound of the Present Invention for Intranasal Administration can be Carried out using techniques as are known in the art.

An effective amount of the compound of the present invention is that amount that decreases microglial activation compared to that which would occur in the absence of the compound; in other words, an amount that decreases the production of neurotoxic and neuromodulatory compounds by the microglia, compared to that which would occur in the absence of the compound. Neuromodulatory refers to a non-lethal alteration in neuron function. The effective amount (and the manner of administration) will be determined on an individual basis and will be based on the specific therapeutic molecule being used and a consideration of the subject (size, age, general health), the condition being treated (AD, acute head injury, cerebral inflammation, etc.), the severity of the symptoms to be treated, the result sought, the specific carrier or pharmaceutical formulation being used, the route of administration, and other factors as would be apparent to those skilled in the art. The effective amount can be determined by one of ordinary skill in the art using techniques as are known in the art. Therapeutically effective amounts of the compounds described herein can be determined using in vitro tests, animal models or other dose-response studies, as are known in the art.

Pharmaceutical preparations of the compounds of the present invention can optionally include a pharmaceutically acceptable diluent or excipient. The compositions may also contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

Treatment Regimen

In practicing the present invention, ApoE analogs may be administered to a subject as a single dose comprising a single-dose-effective amount for preventing hemorrhage growth, and/or for treating complications, or in a staged series of doses which together comprise an effective amount for preventing or treating complications. An effective amount of an ApoE analog refers to the amount of the analog which, when administered in a single dose or in the aggregate of multiple doses, or as part of any other type of defined treatment regimen, produces a measurable statistical improvement in outcome, as evidenced by at least one clinical parameter associated with SAH, ICH, and IVH and/or their complications.

Administration of a single dose refers to administration of an entire dose of an ApoE analog as a slow bolus over a period of less than about 5 minutes. In some embodiments, the administration occurs over a period of less than about 2.5 minutes, and, in some, over less than about 1 min. Typically, a single-dose effective amount comprises at least about 40 µg/kg ApoE analog, such as, at least about 50 µg/kg, 75 µg/kg, or 90 µg/kg, or at least 160 µg/kg ApoE analogs.

It will be understood that the effective amount of an ApoE, as well as the overall dosage regimen, may vary according to the subject's hemostatic status, which, in turn, may be reflected in one or more clinical parameters, including, e.g., relative levels of circulating coagulation factors; amount of blood lost; rate of bleeding; hematocrit, and the like. It will be further understood that the effective amount may be determined by those of ordinary skill in the art by routine experimentation, by constructing a matrix of values and testing different points in the matrix.

For example, in one series of embodiments, the invention encompasses (i) administering a first dose of an ApoE analog; (ii) assessing the subject's coagulation status after a predetermined time; and (iii) based on the assessment, administering a further dose of ApoE analog if necessary. Steps (ii) and (iii) may be repeated until satisfactory hemostasis is achieved.

According to the invention, ApoE analogs may be administered by any effective route, including, without limitation, intravenous, intramuscular, subcutaneous, mucosal, and pulmonary routes of administration. Preferably, administration is by an intravenous route.

The compounds of the present invention can be administered acutely (i.e., during the onset or shortly after events leading to cerebral hemorrhage), or can be administered prophylactically (e.g., before scheduled surgery, or before the appearance of neurologic signs or symptoms), or administered during the course of a degenerative disease to reduce or ameliorate the progression of symptoms that would otherwise occur. The timing and interval of administration is varied according to the subject's symptoms, and can be administered at an interval of several hours to several days, over a time course of hours, days, weeks or longer, as would be determined by one skilled in the art.

In one embodiment, administration of analogs according to the present invention is preferably initiated within about 4 hours after occurrence of the SAH, ICH, and IVH such as, e.g., within about 3 hours, within about 2 hours, or within about 1 hour.

The typical daily regime can be from about 0.01 µg/kg body weight per day, from about 1 mg/kg body weight per day, from about 10 mg/kg body weight per day, from about 100 mg/kg body weight per day, from about 1,000 mg/kg body weight per day. Preferred dosages are between about 0.01 µg/kg and about 10 mg/kg body weight per day, depending on the compound, and more preferably between about 1 mg/kg and about 10 mg/kg body weight per day.

The blood-brain barrier presents a barrier to the passive diffusion of substances from the bloodstream into various regions of the CNS. However, active transport of certain agents is known to occur in either direction across the blood-brain barrier. Substances that can have limited access to the brain from the bloodstream can be injected directly into the cerebrospinal fluid.

Administration of a compound directly to the brain is known in the art. Intrathecal injection administers agents directly to the brain ventricles and the spinal fluid. Surgically-implantable infusion pumps are available to provide sustained administration of agents directly into the spinal fluid. Lumbar puncture with injection of a pharmaceutical compound into the cerebrospinal fluid ("spinal injection") is known in the art, and is suited for administration of the present compounds. Use of PTD domains as described herein and other peptides and non-peptide moieties known in the art may also be used to facilitate transport across the blood-brain barrier.

Pharmacologic-based procedures are also known in the art for circumventing the blood brain barrier, including the conversion of hydrophilic compounds into lipid-soluble drugs. The active agent can be encapsulated in a lipid vesicle or liposome.

The intra-arterial infusion of hypertonic substances to transiently open the blood-brain barrier and allow passage of hydrophilic drugs into the brain is also known in the art. U.S. Pat. No. 5,686,416 to Kozarich et al. discloses the co-administration of receptor mediated permeabilizer (RMP) peptides with compounds to be delivered to the interstitial fluid compartment of the brain, to cause an increase in the permeability of the blood-brain barrier and effect increased delivery of the compounds to the brain.

One method of transporting an active agent across the blood-brain barrier is to couple or conjugate the active agent to a second molecule (a "carrier"), which is a peptide or non-proteinaceous moiety selected for its ability to penetrate the blood-brain barrier and transport the active agent across the blood-brain barrier. Examples of suitable carriers include pyridinium, fatty acids, inositol, cholesterol, and glucose derivatives also add vitamin C. The carrier can be a compound which enters the brain through a specific transport system in brain endothelial cells. Chimeric peptides adapted for delivering neuropharmaceutical agents into the brain by receptor-mediated transcytosis through the blood-brain barrier are disclosed in U.S. Pat. No. 4,902,505 to Pardridge et al. These chimeric peptides comprise a pharmaceutical agent conjugated with a transportable peptide capable of crossing the blood-brain barrier by transcytosis. Specific transportable peptides disclosed by Pardridge et al. include histone, insulin, transferrin, and others. Conjugates of a compound with a carrier molecule, to cross the blood-brain barrier, are also disclosed in U.S. Pat. No. 5,604,198 to Poduslo et al. Specific carrier molecules disclosed include hemoglobin, lysozyme, cytochrome c, ceruloplasmin, calmodulin, ubiquitin and substance P. See also U.S. Pat. No. 5,017,566 to Bodor.

An alternative method of administering peptides of the present invention is carried out by administering to the subject a vector carrying a nucleic acid sequence encoding the peptide, where the vector is capable of entering brain cells so that the peptide is expressed and secreted, and is thus available to microglial cells. Suitable vectors are typically viral vectors, including DNA viruses, RNA viruses, and retroviruses. Techniques for utilizing vector deliver systems and carrying out gene therapy are known in the art. Herpesvirus vectors are a particular type of vector that can be employed in administering compounds of the present invention.

Combination Treatments

The present invention further provides a method of treating, preventing, and ameliorating SAH, ICH, and IVH, comprising administering to a subject in need thereof. ApoE protein or one or more ApoE mimetic peptides in an amount that reduces symptoms of SAH, ICH, and IVH. In practicing the methods of this invention, the therapeutic peptides and/or derivatives thereof may be used alone or in combination with other active ingredients.

The active ingredients may be any active agents that provide a therapeutic benefit to the treatment, prevention and amelioration of cerebral hemorrhage. For example, the ApoE peptides may be used in combination with other therapeutic agents, such as, e.g., oxygen radical scavenging agents such as superoxide dismutase or anti-inflammatory agents such as corticosteroids, hydrocortisone, prednisone and the like; antibacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, gancyclovir, ribavirin, interferons and the like; analgesic agents such as salicylic acid, acetaminophen, ibuprofen, flurbiprofen, morphine and the like; local anesthetics such as lidocaine, bupivacaine, benzocaine and the like; growth factors such as colony stimulating factor, granulocyte-macrophage colony stimulating factor, and the like; antihistamines such as diphenhydramine, chlorphencramine and the like; anti-nausea medications, nutritional additives such as leukovorin, and other like substances.

The present invention may also be used in combination with anti-inflammatory cytokines, growth factors, or leukocyte migration inhibitory compounds. Useful cytokines include, but are not limited to, IL-4, IL-10, IL-11, and IL-13, particularly IL-4 and IL-10, which are known to suppress production of inflammatory cytokines and to be involved in restoring the immune system. Growth factors include GM-CSF among others. These cytokines and growth factors may be administered as purified proteins—obtained naturally or from recombinant sources—or administered in the form of nucleic acids that express these peptides, particularly as fusion proteins.

If desired, one or more agents typically used to treat SAH, ICH, and IVH and cerebral vasospasm may be used as a substitute for or in addition to the therapeutic peptides in the methods and compositions of the invention. Such agents include biologics and small molecule. Thus, in one embodiment, the invention features the combination of an ApoE analog such as a peptide compound comprising a sequence of SEQ ID NO: 1-56 and any of the foregoing agents.

ApoE analogs and other active therapeutic agents may be administered simultaneously or sequentially. When the other therapeutic agents are administered simultaneously they can be administered in the same or separate formulations, but are administered at the same time. The other therapeutic agents are administered sequentially with one another and with inhibitor, when the administration of the other therapeutic agents and the inhibitor is temporally separated. The separation in time between the administration of these compounds may be a matter of minutes or it may be longer.

In some embodiments, the additional active agent comprises an anti-cerebral vasospasm drug. Thus, the present invention includes the use of the disclosed peptides and peptide mimetics in methods and pharmaceutical formulations for the treatment of any of the above diseases or disorders in combination with any known voltage-gated calcium channel blockers including both L-type and R-type voltage-gated calcium channel blockers.

Such voltage-gated calcium inhibitors can be used in combination of the ApoE analogs to treat a subject of a vasospasm or a subject at risk of a vasospasm. A subject at risk of a vasospasm includes a subject who has detectable blood in the cerebrospinal fluid, or one who has a detectable aneurysm as detected by a CT scan, yet has not begun to experience the symptoms associated with having a vasospasm. A subject at risk of a vasospasm may also be one who has experienced a traumatic head injury. Traumatic head injury usually results from a physical force to the head region, in the form of a fall or a forceful contact with a solid object. Subjects at risk of a vasospasm may also include those who have recently (e.g., in the last two weeks or months) experienced a subarachnoid hemorrhage (as described above).

In one aspect of the invention, an R-type voltage-gated calcium channel inhibitor is administered to the subject having or at risk of having a vasospasm in an effective amount to treat a vasospasm. An effective amount to treat a vasospasm may be that amount necessary to ameliorate, reduce or eliminate altogether one or more symptoms relating to a vasospasm, preferably including brain damage that results from vasospasm such as an infarct. Brain damage can be measured anatomically using medical imaging techniques to measure infarct sizes. Alternatively or in conjunction, brain damage may be measured functionally in terms of cognitive or sensory skills of the subject.

Subjects at risk of vasospasm are currently administered a variety of preventative medications including L-type voltage-dependent calcium channel (L-type VDCC) inhibitors (e.g., nimodipine), phenylephrine, dopamine, as well as a combination of mannitol and hyperventilation. Some forms of prophylactic treatments aim to increase the cerebral perfusion pressure. In accordance with the present invention, any of these prophylactic therapies may be co-administered to a subject at risk of having a vasospasm along with the agents of the invention. Thus, other therapeutic agents include but are not limited to anti-cerebral vasospasm drug such as L-type VDCC and a phenylalkalamine such as verapamil, etc.

An L-type voltage-dependent calcium channel inhibitor as used herein as a calcium entry blocking drug whose main pharmacological effect is to prevent or slow the entry of calcium into cells via L-type voltage-gated calcium channels. Examples of L-type calcium channel inhibitors include but are not limited to: dihydropyridine L-type blockers such as nisoldipine, nicardipine and nifedipine, AHF (such as 4aR, 9aS)-(+)-4a-Amino-1,2,3,4,4a,9a-hexahydro-4-aH-fluorene, HCl), isradipine (such as 4-(4-Benzofurazanyl)-1,-4-dihydro-2,6-dimethyl-3,5-pyridinedicarboxylic acid methyl 1-methhylethyl ester), Calciseptin/calciseptine (such as isolated from (*Dendroaspis polylepis polylepis*, H-Arg-Ile-Cys-Tyr-Ile-His-Lys-Ala-Ser-Leu-Pro-Arg-Ala-Thr-Lys-Thr-Cys-Val-Glu-Asn-Thr-Cys-Tyr-Lys-Met-Phe-Ile-Arg-Thr-Gln-A-rg-Glu-Tyr-Ile-Ser-Glu-Arg-Gly-Cys-Gly-Cys-Pro-Thr-Ala-Met-Trp-Pro-Tyr-Gl-n-Thr-Glu-Cys-Cys-Lys-Gly-Asp-Arg-Cys-Asn-Lys-OH (SEQ ID NO:57), Calcicludine (such as isolated from *Dendroaspis angusticeps* (eastern green mamba)), (H-Trp-Gln-Pro-Pro-Trp-Tyr-Cys-Lys-Glu-Pro-Val-Arg-Ile-Gly-Ser-Cys-Lys-Lys-Gln-Phe-Ser-Ser-P-he-Tyr-Phe-Lys-Trp-Thr-Ala-Lys-Lys-Cys-Leu-Pro-Phe-Leu-Phe-Ser-Gly-Cys-Gl-y-Gly-Asn-Ala-Asn-Arg-Phe-Gln-Thr-Ile-Gly-Glu-Cys-Arg-Lys-Lys-Cys-Leu-Gly-Lys-OH, SEQ ID NO:58), Cilnidipine (such as also FRP-8653, a dihydropyridine-type inhibitor), Dilantizem (such as (2S, 3S)-(+)-cis-3-Acetoxy-5-(2-dimethylaminoethyl)-2,3-dihydro-2-(4-metho-xyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro- 2-(4-methoxyphenyl), (+)-cis-, monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from *Dendroaspis polylepis polylepis* venom), FTX-3.3 (such as an isolate from *Agelenopsis aperta*), Neomycin sulfate, Nicardipine (such as 1,4-Dihydro-2,6-dimethyl-4-(3-nitrophenyl)methyl-2-[methyl(phenylmethyl)a-mino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4a,5-dimethyl-2-o-xo-6-naphthyl]Z-3'-methylthio-1'-propenoate), Phloretin (such as 2',4',6'-Trihydroxy-3-(4-hydroxyphenyl) propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine, SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (+/−)-Methoxyverapamil or (+)-Verapamil (such as 5-[N-(3,4-Dimethoxyphenylethyl)methylamino]-2-(3,4-dimethoxyphenyl)-2-iso-propylvaleronitrile hydrochloride), and (R)-(+)-Bay K8644 (such as R-(+)-1,4-Dihydro-2,6-dimethyl-5-nitro-4-[2-(trifluoromethyl)phenyl]-3-pyridinecarboxylic acid methyl ester). The foregoing examples may be specific to L-type voltage-gated calcium channels or may inhibit a broader range of voltage-gated calcium channels, e.g. N, P/Q, R, and T-type.

It will be understood that, in embodiments comprising administration of combinations of ApoE analogs with other agents, the dosage of ApoE analogs may on its own comprise an effective amount and additional agent(s) may further augment the therapeutic benefit to the subject. Alternatively, the combination of ApoE analogs and the second agent may together comprise an effective amount for preventing vasospasm complications associated with SAH, ICH, and IVH. It will also be understood that effective amounts may be defined in the context of particular treatment regimens, including, e.g., timing and number of administrations, modes of administrations, formulations, etc.

Treatment Outcomes

In practicing the present invention, the severity of SAH, ICH, and IVH and their complications may be assessed using conventional methods, such as, e.g., Imaging by CT or MR scans or the Clinical assessment scores. Assessments may be performed at least about 15 days from the start of treatment according to the invention, such as, e.g., at least about 30 days, at least about 40 days, or at least about 90 days from the start of treatment.

Methods for testing organ function and efficiency, and suitable biochemical or clinical parameters for such testing, are well known to the skilled clinician.

Such markers or biochemical parameters of organ function are, for example: Brain perfusion: Measurements of cerebral blood flow Brain metabolism: Measurements of cerebral oxygen extraction or direct measurements of cerebral metabolic rate of oxygen. Measurement of other substrates than oxygen such as glucose are also included. Brain integrity: MRI (any and all standardized protocol sequences), CT, CTA, MRA Brain cell electrical function as measured by EEG Brain function by well established neurological tests (e.g., Microdialysis, Transcranial Doppler).

Methods for testing for coagulopathy and inflammation are also well known to the skilled clinician. Such markers of a coagulapathic state are, for example, PTT, Fibrinogen depletion, elevation in TAT complexes, ATIII activity, IL-6, IL-8, or TNFR-1.

In the present context, prevention includes, without limitation, the attenuation, elimination, minimization, alleviation or amelioration of one or more symptoms or conditions associated with SAH, IVH, ICH and/or their complications, including, but not limited to, the prevention of further damage to and/or failure of the effected organ already subject to some degree of organ failure and/or damage, as well as the prevention of damage and/or failure of further organs not yet subject to organ failure and/or damage. Examples of such symptoms or conditions include, but are not limited to, morphological/structural damage and/or damage to the functioning of organs such as, but not limited to, brain and surrounding organs. Examples of such symptoms or conditions include, but are not limited to, morphological/structural damage and/or damage to the functioning of the organ(s) such as, for example, accumulation of proteins or fluids due to mass effect of the hematoma or from resulting inflammatory reactions in the surrounding tissue, tissue necrosis, fibrin deposition, hemorrhage, edema, or inflammation.

Attenuation of organ failure or damage encompasses any improvement in organ function as measured by at least one of the well known markers of function of said organ compared to the corresponding value(s) found in SAH, IVH, and ICH subjects not being treated in accordance with the present invention.

This invention is further illustrated by the following examples which should not be construed as limiting. The contents of all references, patents, and published patent applications cited throughout this application, as well as the figures, are incorporated herein in their entirety by reference.

EXAMPLES

Materials and Methods
Therapeutic Agents

Nimodipine was obtained from the Duke University Medical Center Pharmacy in 30-mg/ml capsules. Each capsule was opened and the contents were diluted with 0.9% NaCl until the desired concentrations (0.67 mg/ml and 0.33 mg/ml) were reached. The solutions were stored in a dark area in accordance with manufacturer recommendations. The carboxyamidotriazole (CAI) was obtained with permission from the National Institutes of Health. It was dissolved in polyethylene glycol and diluted to appropriate concentrations (2.08 mg/ml and 0.83 mg/ml. The solutions were refrigerated at 4° C. The 1410-D apoE-derived peptide, acetyl-AS-Aib-LRKL-Aib-KRLL-amide (SEQ. ID. NO. 7), was synthesized in the Peptide Synthesis Laboratory at the University of North Carolina (Chapel Hill, N.C.) to a purity of 95% and diluted in isotonic saline as previously described (Gao et al. 2006; Laskowitz et al. 2006).

Murine Model of SAH

Given the limited understanding of the pathophysiology of vasospasm and the pressing clinical need for more effective approaches, the use of clinically relevant animal models of SAH remains extremely important. A variety of animal models have been developed. Nosko and colleagues (Nosko et al., 1985) studied the effects of nimodipine on chronic vasospasm in monkeys and, using their model, produced results similar to those found in clinical trials. No difference in the incidence and severity of delayed vasospasm in a rabbit model was attributed to the use of nimodipine in a study in which dynamic perfusion computed tomography imaging was used (Laslo et al. 2006). In both animal studies angiographically determined end points were used and the conclusions were similar to those of human clinical trials; however, neither study incorporated the behavioral outcomes of the animals, a limitation found in many studies involving animal models of SAH.

Recently, a murine model of SAH has been characterized that demonstrates evidence of vascular proliferation, lumen narrowing, and functional impairments (Parra et al., 2002). The clinical relevance of this model in testing new therapeutic approaches was suggested by the finding that the protective effects of simvastatin on murine vasospasm were readily translatable to the clinical arena (Lynch et al., 2005; McGirt et al. 2002). One advantage of using a murine model is the availability of transgenic technology that can be used to differentiate the molecular mechanisms of disease. For example, recent studies involving endothelial nitric oxide synthase knockout transgenic animals demonstrated that the palliative effects of statins in the presence of SAH were dependent on upregulation of endothelial nitric oxide synthase (McGirt et al., 2005).

Subarachnoid hemorrhage was produced using the method previously described by Parra, et al. (2002). Male C57B1/6J mice, 12 to 14 weeks of age, were placed in a chamber and anesthetized by administering a gas mixture containing isoflurane. The trachea was intubated and the lungs mechanically ventilated with a mixture of 1.6% isoflurane in 30% $O_2$/balance $N_2$. A midline incision was made in the neck, and the right common CA was exposed. The external CA was then exposed and ligated, leaving a small stump attached to the common CA. A blunted 5-0 monofilament nylon suture, 10 mm in length, was introduced into the external CA stump and advanced into the internal CA to a point just distal to the bifurcation of the ACA and MCA in the circle of Willis. Here resistance was encountered and the suture was advanced 3 mm further to perforate the right ACA, resulting in subarachnoid bleeding. The suture was removed, hemostasis was ensured, and the skin was closed.

For the CAI experiment, the mice were randomly assigned to one of three groups: high-dose CAI (250 mg/kg/day), low-dose CAI (100 mg/kg/day), or vehicle treatment. The CAI was administered by oral gavage immediately postoperatively and every 8 hours thereafter until postoperative Day 3. In the combined nimodipine-apoE peptide experiment, the mice were randomized to five groups: high-dose nimodipine (8 mg/kg/day), low-dose nimodipine (4 mg/kg/day), high-dose nimodipine plus apoE-mimetic peptide (1.2 mg/kg/day), the peptide alone (1.2 mg/kg/day), or vehicle treatment. The peptide dose was selected based on the optimum dose determined in a previous study (Gao et al., 2006), whereas the two nimodipine doses were chosen based on standard dosages used in clinical practice. The apoE-mimetic peptide was given intravenously immediately postoperatively and every 12 hours thereafter until the mice were killed on postoperative Day 3. Nimodipine was given via oral gavage immediately postoperatively and every 8 hours thereafter. Behavioral analysis was conducted by performing a rotarod test, and a neurological severity score was assigned to each animal every day. After the behavioral assessment had been made on Day 3, the mouse was killed and its vasculature was perfused with an India ink-gelatin mixture. The dead animal was refrigerated for 24 hours, after which its brain was removed and the diameter of the right MCA was measured.

Neurological Evaluation Following SAH

Behavioral outcomes were assessed by an observer blinded to animal group assignment who used a neurological severity scale (Yokoo et al., 2004) (score range 3-21) and rotarod testing (Lynch et al., 2005). On the day before surgery, baseline rotarod data and neurological severity scores were obtained for all mice. The rotarod data were collected by first placing the mice on the apparatus (Ugo Basile, Comerio, Italy) for a 300-second training period with the rotarod set in the accelerating rotational speed mode. Afterward, using this accelerating rotational speed mode, rotarod latencies were recorded for three trials per mouse. A neurological severity score was then assigned. The score was based on an assessment of motor components derived from spontaneous activity, symmetry of limb movements, climbing, and balance and coordination, with each component being scored from 0 to 3. Sensory components were used to analyze body proprioception and tactile and vibrissa responses to stimuli. These components were scored from 1 to 3. Assignment of the neurological severity score and the rotarod analysis (minus the initial training portion) were repeated daily for 3 days postoperatively.

Blood Pressure Measurements

Blood pressure was measured over a 120-minute period after administration of each drug or drug combination, in a separate animal cohort. Following administration of the drug(s), the mouse underwent tracheal intubation and anesthesia was induced using an isoflurane mixture. The femoral artery was cannulated via a small incision in the right groin. Blood pressure measurements were recorded every minute for the first 10 minutes and then every 5 minutes for the remaining 110 minutes.

Cerebral Vascular Perfusion and MCA Diameter after SAH

After the behavioral examination had been completed on postoperative Day 3, cerebral vascular perfusion was performed as described previously (Gao et al., 2006; Parra et al., 2002). Each mouse was placed in a chamber and isoflurane was administered to induce anesthesia. The animal's trachea was intubated and its chest opened to allow cannulation of the proximal aorta.

Plastic tubing (3.22-mm internal diameter) was used to deliver infusion solutions in a pulsatile manner (McGirt et al., 2005; Parra et al., 2002). Thirty milliliters of 0.9% NaCl, 20 ml of 10% formalin, and 10 ml of India ink-gelatin mixture were infused in that order. The dead mouse was refrigerated for 24 hours to ensure solidification of the gelatin within the vasculature. Following refrigeration, the mouse brain was harvested and stored in 10% formalin. The cerebral vasculature was photographed using a video-linked dissecting microscope controlled by an image analyzer (MCID Elite; Interfocus Imaging, Linton, United Kingdom). The diameter of the right MCA at the site 1 mm distal to the MCA-ACA bifurcation was recorded using digital measurement techniques.

Statistical Analysis

Rotarod latencies and neurological severity scores were compared using repeated-measures analysis of variance with time as the repeated variable. When the resulting F values were greater than 1, the Student t-test was used to compare drug-treated groups with the vehicle-treated group. The diameters of the MCA lumina were also compared using the unpaired Student t-test.

Example 1

Effect of CAI on SAH Outcome

Given the vasoactive nature of the drugs used and the potential confounding effects of hypotension, the hemo-dynamic effects of high-dose CAI, nimodipine, and apoE-mimetic peptide were tested in surrogate animals. No significant changes were observed after administration of any of these drugs or drug combinations.

To test the effect of CAI as a possible therapy to reduce vasospasm, vehicle (16 animals), low-dose CAI (100 mg/kg/day; 16 animals), or high-dose CAI (250 mg/kg/day; 12 animals) was administered after induction of SAH. A significant decrease in rotarod latency (that is, the time the animal remains on the rotating bar) was observed following administration of high-dose CAI compared with administration of vehicle (mean latency for animals receiving high-dose CAI 90±18 seconds; mean latency for animals receiving vehicle 180±17 seconds; p=0.0008) (FIG. 1A). The neurological severity scores paralleled the results of the rotarod tests (FIG. 1B).

Figure 2:
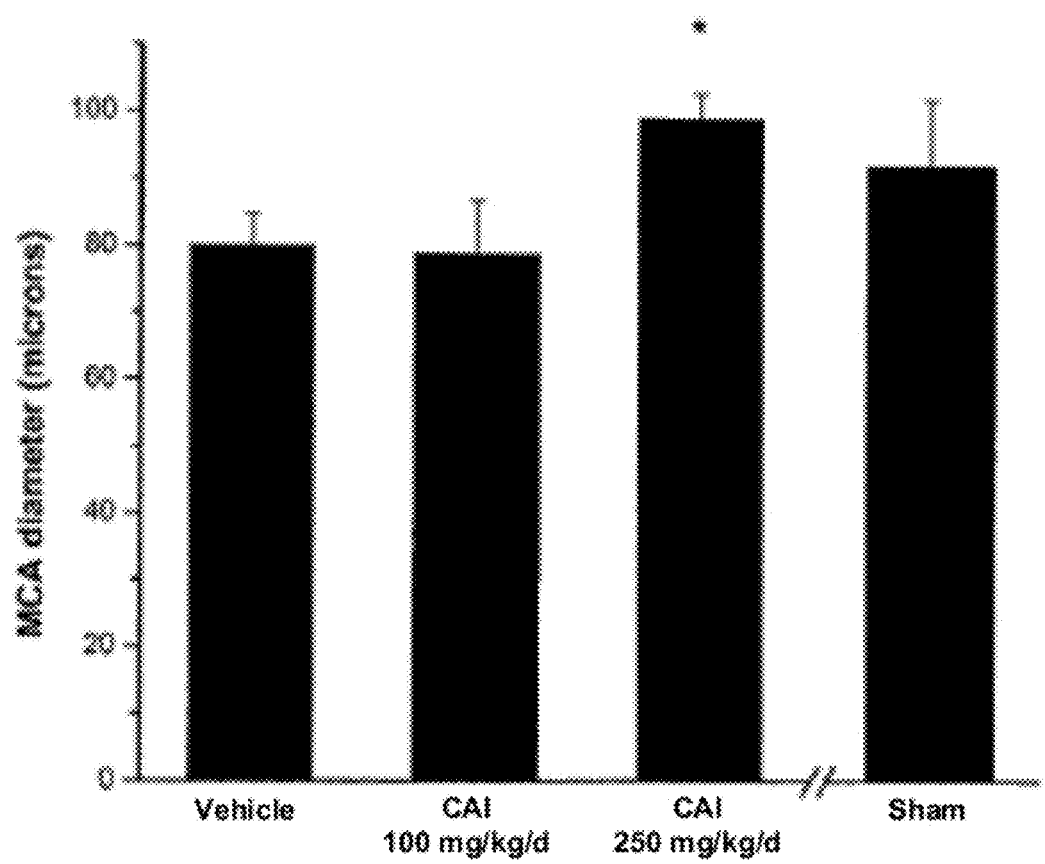
FIG. 2 is a bar graph showing that administration of high-dose CAI causes a significant increase in the MCA lumen diameter compared with vehicle treatment. The inclusion of data for sham-operated animals is for illustrative purposes only; this group was not included in the statistical analysis. *$p<0.05$.

The diameters of the right MCA lumina are summarized in FIG. 2. A significant increase in MCA diameters was observed when the high-dose CAI-treated group (mean diameter 99±4 μm) was compared with the vehicle-treated group (mean diameter 80±4 μm; p=0.0191).

Example 2

Effect of Nimodipine on SAH Outcome

In this experiment, mice were treated with vehicle (11 animals), low-dose nimodipine (4 mg/kg/day; 11 animals), or high-dose nimodipine (8 mg/kg/day; 11 animals) after induction of SAH.

Figure 3:
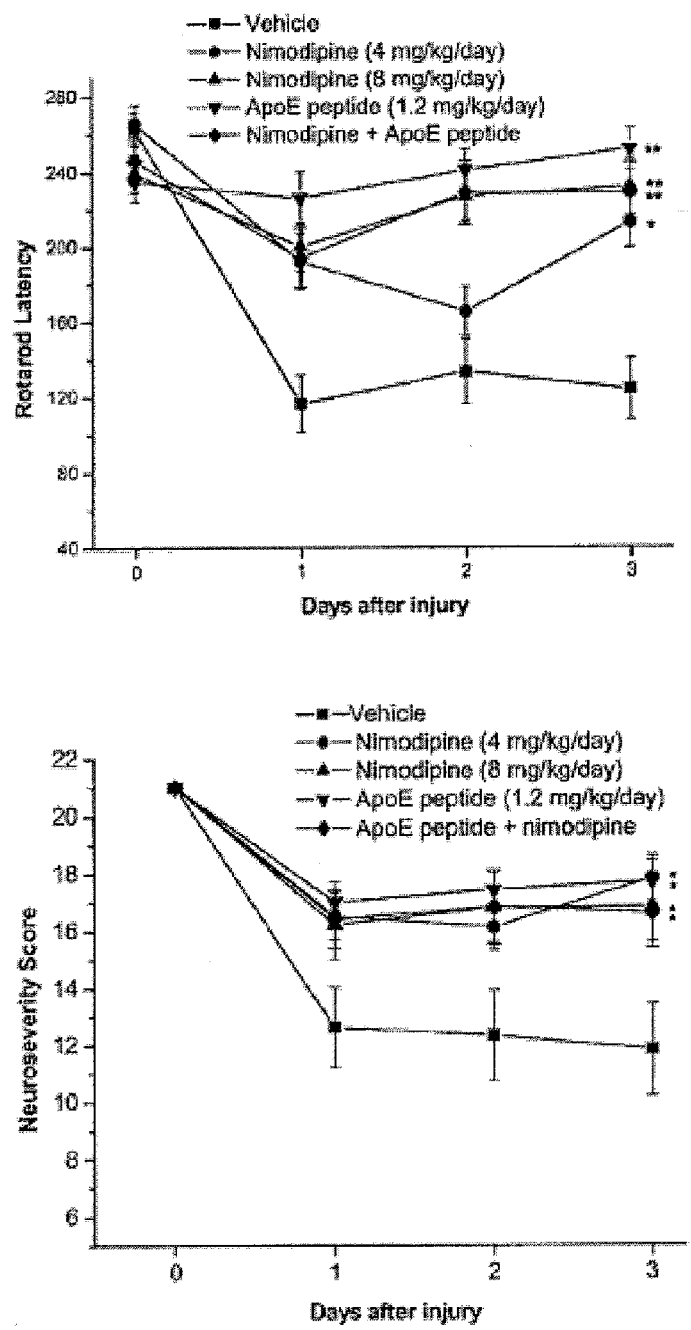
FIG. 3 is a line graph showing the effects of drugs on rotarod latency and neurological severity scores. Upper: An assessment of rotarod latencies after SAH shows significant improvements in drug-treated animals compared with vehicle-treated animals. Lower: Groups of animals treated with high-dose nimodipine (8 mg/kg/day), low-dose nimodipine (4 mg/kg/day), apoE-mimetic peptide, and the combination of nimodipine and peptide had significantly improved neurological severity scores compared with the vehicle-treated group. *$p<0.05$; **$p<0.01$.

Rotarod latencies for both the high-dose nimodipine-treated group (mean latency 231±15 seconds) and the low-dose nimodipine-treated group (mean latency 213±13 seconds) were significantly higher than those of the vehicle-treated group (mean latency 124±16 seconds; p<0.0001 and p=0.0068, respectively). Significant differences in neurological severity scores were also observed between the treatment groups (mean score in the high-dose nimodipine-treated group was 17±1 and that in the low-dose nimodipine-treated group was 18±1) and the vehicle-treated group (mean score 12±2; p<0.05; FIG. 3).

Figure 4:
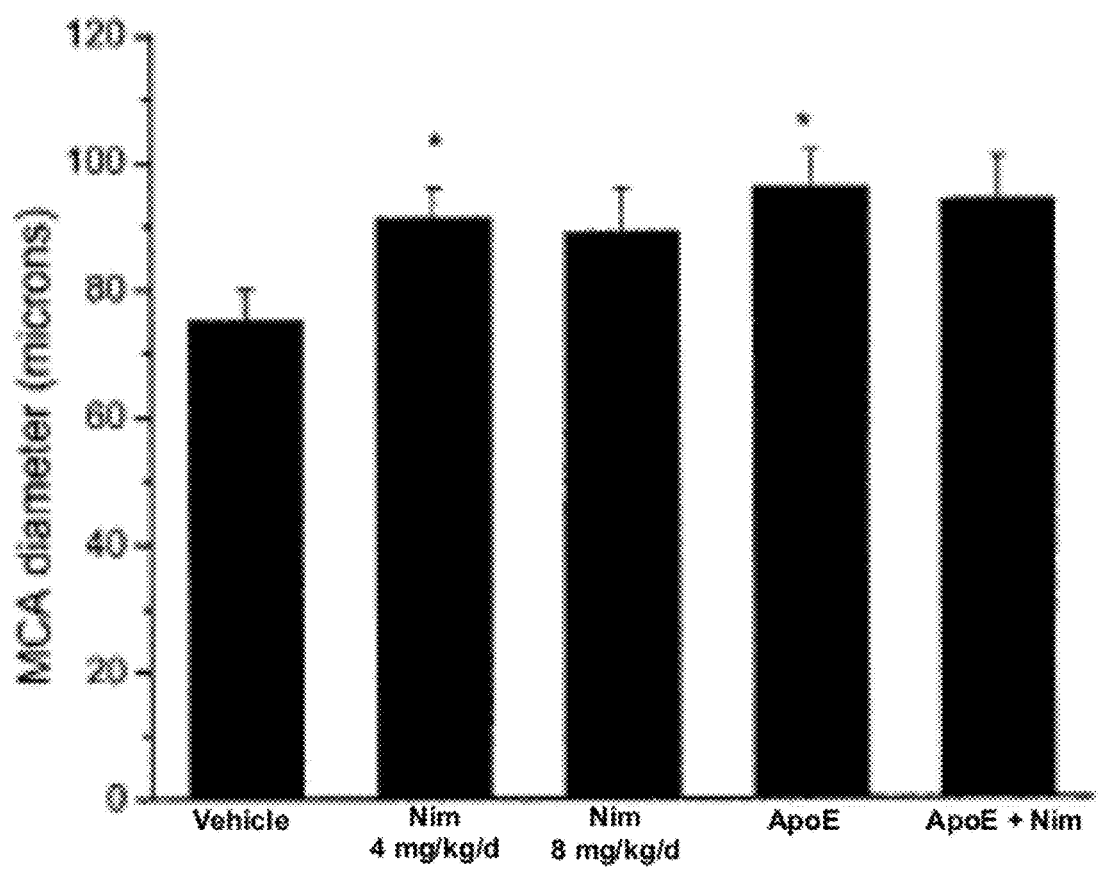
FIG. 4 is a bar graph demonstrating differences in the diameters of the MCA lumina. In a comparison of the four drug treatment groups with the vehicle-treated group in the nimodipine/apoE-mimetic peptide experiment, only the low-dose nimodipine- and the peptide-treated groups had increased MCA diameters. *$p<0.05$.

Although both doses of nimodipine significantly improved behavioral outcomes, a significant improvement in MCA diameters was only identified in the group treated by the low dose. The mean diameter in the low-dose nimodipine-treated group was 91±5 μm and that in the vehicle-treated group was 74±5 (p=0.034). The mean diameter in the high-dose nimodipine group was 89±7 μm (FIG. 4).

Example 3

Effect of apoE-Mimetic Peptide on SAH Outcome

The next goal of this study was to examine the effects of administration of apoE-mimetic peptide in the murine SAH model. Based on previous studies, the optimum dose of the peptide has already been determined in this model, and thus only two groups of animals were used, mice treated with vehicle (11 animals) and those treated with peptide (1.2 mg/kg/day; 11 animals). The peptide-treated group performed significantly better than the vehicle-treated group on the rotarod test and on tests of neurological severity (p<0.001 and p=0.0040, respectively; FIG. 3). In addition to improvements in behavioral outcomes, there was a significant increase in the diameters of the right MCA lumina in the peptide-treated group (mean diameter 97±6 μm) compared with the vehicle-treated group (mean diameter 74±5 μm; p=0.02; FIG. 4).

Example 4

Effect of Nimodipine Plus apoE-Mimetic Peptide on SAH Outcome

Because nimodipine is currently used to treat SAH patients, it is important to characterize the interactions between nimodipine and any new therapeutic agent, as any new treatment will probably be administered in combination with nimodipine in the clinical setting. For this portion of the experiment two groups were compared: one treated with vehicle (11 animals) and the other treated with both nimodipine and peptide (nimodipine 8 mg/kg/day, peptide 1.2 mg/kg/day; 11 animals). This combined treatment significantly improved both rotarod latency (229±16 seconds) and the neurological severity score (17±1) compared with vehicle treatment (p<0.0001 and p=0.0216, respectively; FIG. 3). The behavioral outcomes in this combination group were not significantly different from those observed in the other treatment groups. In addition, a significant difference was not present between the diameters of the MCA lumina in the two groups (FIG. 4).

Examples 1-4 demonstrate that clinically relevant doses of nimodipine improved behavioral outcomes in this mouse SAH model without causing any dose-dependent change in the diameters of the MCA lumina. In contrast, the apoE-mimetic peptide improved behavioral outcomes and increased the diameters of the MCA lumina when compared with vehicle. Finally, high-dose CAI worsened functional outcomes, although it increased the diameters of the MCA lumina.

Although nimodipine treatment is the standard of care in clinical practice following aneurysmal SAH, its efficacy has been studied in relatively few animal models of SAH (Lasko et al., 2006; Nosko et al. 1985). In general, investigators have evaluated angiographic vasospasm rather than behavioral outcome. To increase the clinical relevance of the murine SAH model, two end points were incorporated: angiographic findings and behavioral outcomes. Although both low- and high-dose nimodipine treatment improved behavioral outcome, only the low dose of the drug was associated with a significant reduction in vasospasm. This is consistent with the results of clinical studies of nimodipine in patients with SAH, which have failed to demonstrate a consistent reduction in angiographically determined vasospasm despite improved functional outcome (Allen et al., 1983; Petruck et al., 1988; Pickard et al., 1989). This dissociation between improved lumen diameter and functional outcome suggests that, in addition to its vasoactive effects, nimodipine may be directly neuroprotective via its effect on voltage-gated neuronal calcium channels.

To explore this possibility further, animals were treated with CAI, which acts solely on non-voltage-gated calcium channels. Although CAI would be expected to have comparable vasodilatory effects on cerebral vessels, it would not be expected to have any direct effect on neuronal calcium channels. It is demonstrated that, although treatment with CAI significantly enlarged the MCA lumen without hemodynamic compromise, the drug was associated with worse functional outcome than vehicle alone.

These results suggest that nimodipine may be acting at the neuronal level to block calcium influx. In fact, there is preclinical evidence suggesting that nimodipine is effective in instances of acute cerebral ischemia (Inzitari et al., 2005; Korenkov et al., 2000). It is possible that the failure of nimodipine to improve stroke outcome in clinical trials is related to the delayed onset of drug administration in the clinical setting. Nevertheless, aneurysmal SAH represents a unique opportunity to initiate neuroprotective treatment before the onset of ischemia, which most often occurs within the first several weeks posthemorrhage. This delayed ischemia creates a window of opportunity during which neuroprotective interventions can be prophylactically administered.

These results suggest a dissociation between changes in the diameter of the MCA lumen and functional improvement, and this is consistent with the findings of several clinical trials (Allen et al., 1983; Haley et al., 1993a; Haley et al., 1993b; Pickard et al., 1989). The possibility that surrogate radiographic evidence of vasospasm may not be predictive of functional outcome should be considered in the design of clinical trials in which new therapies for SAH are evaluated.

The results of the study confirm that intravenous administration of the apoE-mimetic peptide was well tolerated, improved functional outcomes, and reduced evidence of vasospasm following SAH. They also demonstrated that the apoE peptide was well tolerated when coadministered with nimodipine, and was at least as effective as nimodipine alone.

Following treatment, animals receiving SAH performed nearly as well as sham controls in the behavioral tests of rotarod latency and clinical neurological severity. This ceiling effect precluded detection of any possible additive benefit of the apoE-nimodipine combination over nimodipine alone. Given that long-term neurocognitive deficits are common in patients with SAH, incorporating longer-term tasks of learning and memory might improve the utility of this model in terms of evaluating long-term synergistic effects.

Example 5

Figure 5:
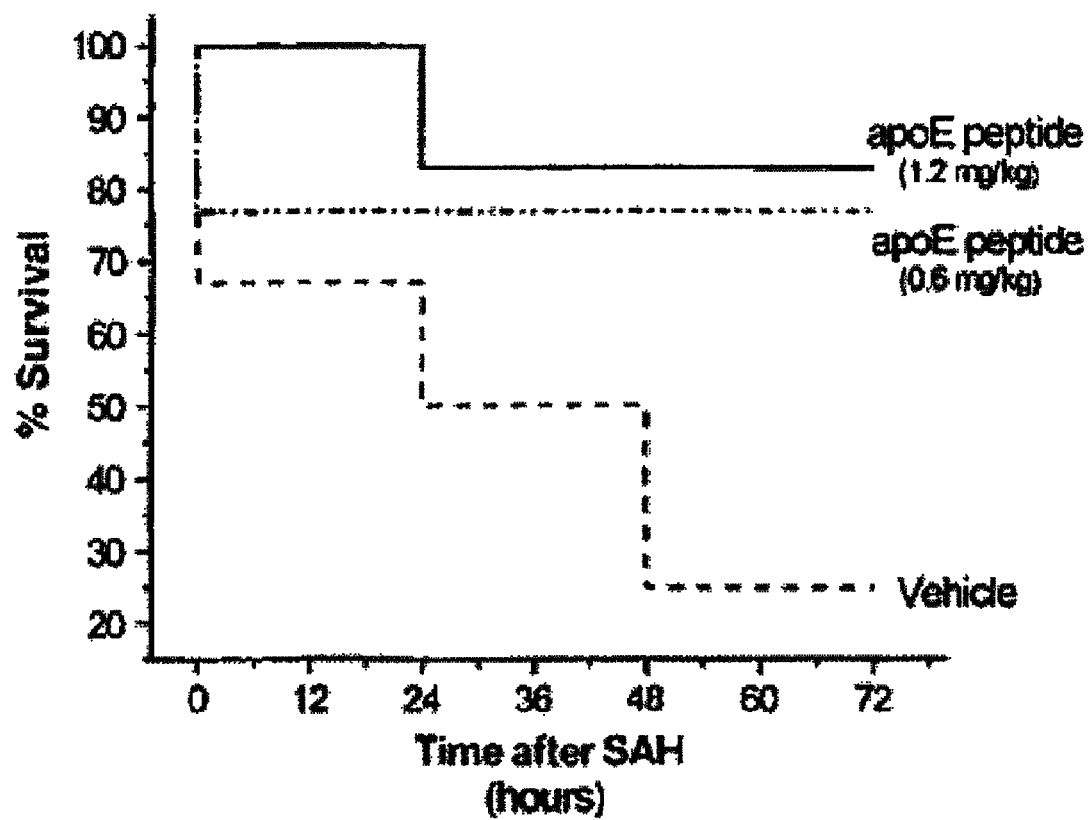
FIG. 5 is a graph showing the effect of ApoE-1410 on animal mortality. Following subarachnoid hemorrhage (SAH), animals were randomized to receive either vehicle, low-dose apoE 1410; or high-dose apoE 1410 administered in 100 μL isotonic saline and delivered intravenously by tail vein twice daily for 3 days following injury. Treatment with apoE 1410 resulted in a significant decrease in mortality ($p<0.01$ for both treated groups versus vehicle).
Figure 6:
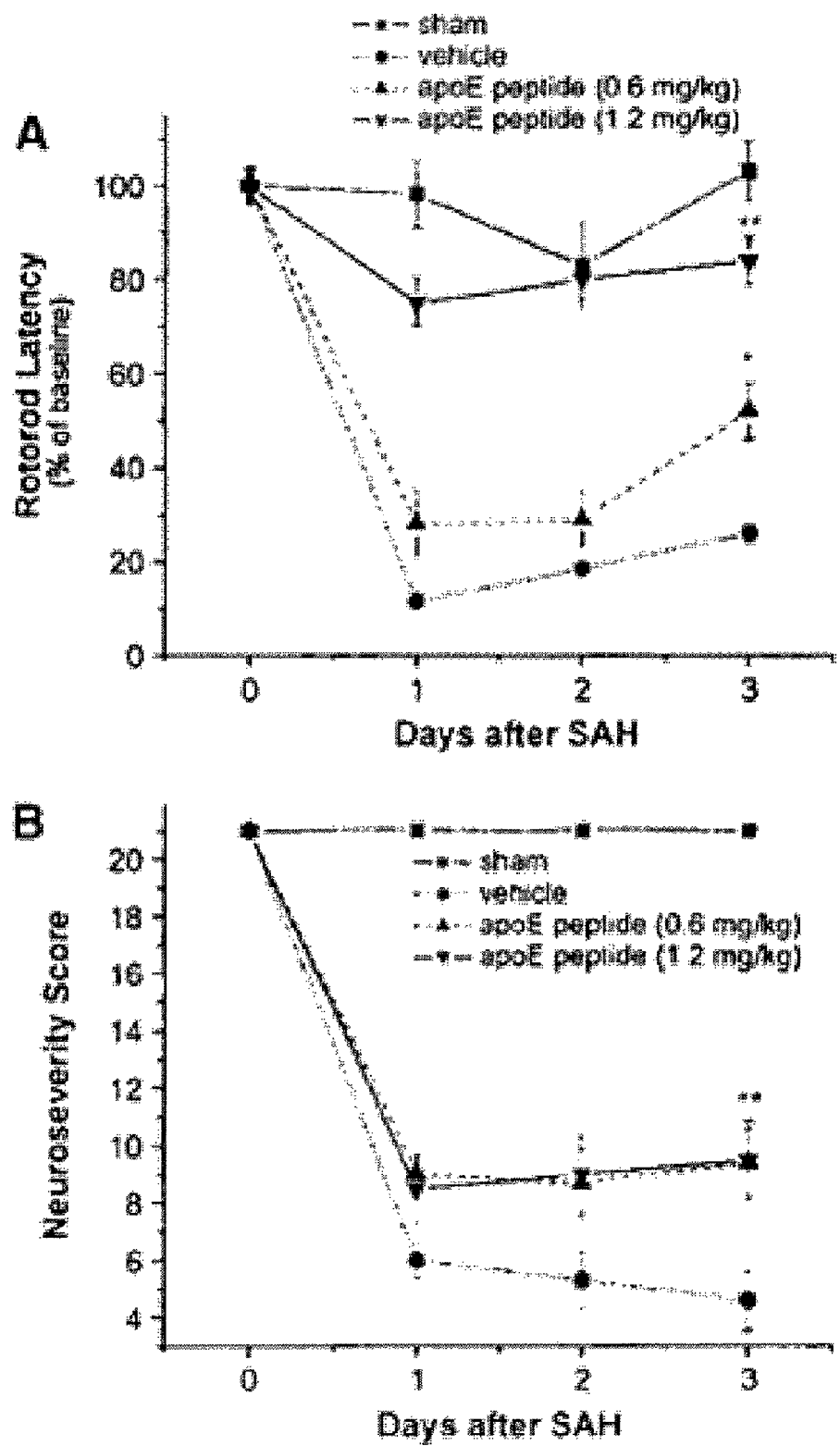
FIG. 6 is a graph showing the effect of ApoE-1410 on functional outcome in a murine SAH model. In panel (A), animals treated with apoE 1410 had dose-dependent improvement in Rotorod performance following subarachnoid hemorrhage (SAH) (*$p<0.01$ low dose versus vehicle; $p<0.01$ high dose versus vehicle). In panel (B), functional improvement was also demonstrated by serial neurological clinical assessments ($p<0.01$ in both treated groups versus vehicle). Sham-operated animals (no SAH) are provided for normal reference values and were not included in statistical analysis.
Figure 7:
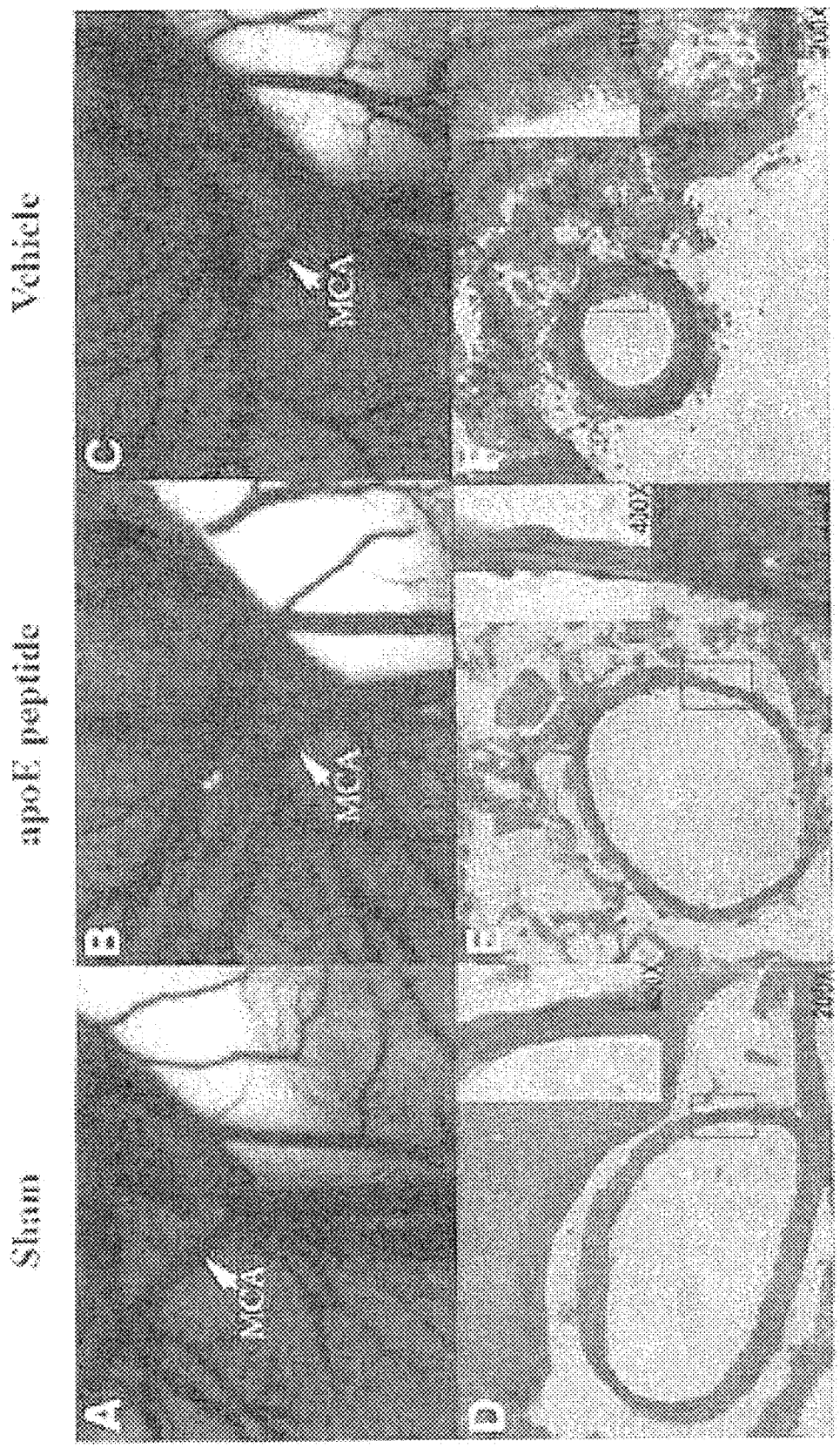
FIG. 7 is a graph showing the effect of ApoE-1410 on vasospasm in a murine SAH model. Representative India ink/gelatin casting (A-C) and hematoxylin & eosin (D-F) photomicrographs performed 72 hours after induction of experimental subarachnoid hemorrhage (SAH) reveals hemorrhage in the basilar cisterns. Vasospasm, defined as the reduction of middle cerebral artery (MCA) diameter was attenuated in the group treated with apoE peptide (B, E). Sham-treated animals had no evidence of vasospasm or morphological changes in the vessel wall (A, D) as compared with animals with SAH that were treated with vehicle, which demonstrated significant luminal narrowing (C) associated with increased thickness of the vessel wall and corrugation of the internal elastic membrane (F).

Effect of ApoE-Mimetic Peptide on Functional Outcome, Mortality, and Vasospasm in a murine SAH Model To test the effect of apoE-1410 as a possible therapy, either vehicle (n=21 animals), low-dose ApoE-1410 (0.6 mg/kg; n=14 animals), or high-dose ApoE-1410 (1.2 mg/kg; n=16 animals) was administered to 12- to 14-week-old male C57B1/6 mice after SAH. Both drug and vehicle were administered intravenously by tail vein immediately following SAH and at 12-hour intervals for the next 72 hours. Administration of the apoE mimetic caused a significant decrease in mortality ($p<0.01$), an effect that was dose-dependent (FIG. 5). Animals treated with the apoE peptide also had better functional outcomes at 72 hours (FIG. 6). Those reductions in morbidity and improvements in function were associated with a significant reduction in MCA vasospasm in the treated group (MCA diameter 98.1±30.6 µM in peptide group versus 70.5±37.2 µM in vehicle group. $P<0.05$ (FIG. 7).

In the study, the smaller 12 residue apoE-mimetic peptide Ac-AS-Aib-LRKL-Aib-KRLL-amide (SEQ. ID. NO. 7; apoE-1410) was tested. This peptide contains two Aib substitutions, at positions L140 and R145 of apoE (133-149). Aib is a non-natural amino acid that has been shown to enhance helical conformations regardless of the amino acid types present in the peptide (Marshall et al. Proc. Natl. Acad. Sci. USA, 87:487-49, 1990). In addition, Aib improves binding affinity because it exhibits a reduction in conformational entropy loss on binding, relative to other amino acids (Ratnaparkhi et al. Protein Eng. 12:697-702, 2000). ApoE-1410 exhibited enhanced activity as compared to apoE (133-149) in an in vitro assay of microglial suppression. See PCT/US05/31431, which is herein incorporated by reference. When administered following SAH in a clinically relevant paradigm (every 12 hours for 3 days), peptide treatment was associated with a substantial reduction in mortality and vasospasm. This was associated with a reduction in functional deficit as assessed by daily neuro-severity scores and Rotorod testing.

LITERATURE CITED

All references and patents cited herein are herein incorporated by reference in their entireties, including, but not limited to, the following:

1. Allen G S, Ahn H S, Preziosi T J, Battye R, Boone S C, Chou S N, et al: Cerebral arterial vasospasm—a controlled trial of nimodipine in patients with subarachnoid hemorrhage. N Engl J Med 308:619-624, 1983
2. Bauer K S, Figg W D, Hamilton J M, Jones E C, Premkumar A, Steinberg S M, et al: A pharmokinetically guided Phase II study of carboxyamido-triazole in androgen-independent prostate cancer. Clin Cancer Res 5:2324-2329, 1999
3. Franklin A J, Jetton T L, Kuchemann C L, Russell S R, Cohn E C: CAI is a potent inhibitor of neovascularization and imparts neuroprotection in a mouse model of ischemic retinopathy, Invest Ophthalmol Vis Sci 45:3756-3766, 2004
4. Friedman G, Froom P, Sazbon L, Grinblatt I, Shochina M, Tsenter J, et al: Apolipoprotein E-ε4 genotype predicts poor outcome in survivors of traumatic brain injury. Neurology 52:244-247, 1999
5. Gao J, Wang H, Sheng H, Lynch J R, Warner D S, Durham L, et al: A novel apoE-derived therapeutic reduces vasospasm and improves outcome in a murine model of subarachnoid hemorrhage. Neurocrit Care 4:25-31, 2006
6. Haley E C Jr, Kassell N F, Torner J C: A randomized controlled trial of high dose intravenous nicardipine in aneurysmal subarachnoid hemorrhage, A report of the Cooperative Aneurysm Study. J Neurosurg 78:537-547, 1993
7. Haley E C Jr, Kassell N F, Torner J C: A randomized trial of nicardipine in subarachnoid hemorrhage: angiographic and transcranial Doppler ultrasound results. A report of the Cooperative Aneurysm Study. J Neurosurg 78:548-553, 1993
8. Hanel R A, Xavier A R, Mohammad Y, Kirmani J F, Yahia A M, Qureshi A I: Outcome following intracerebral hemorrhage and subarachnoid hemorrhage, Neurol Res 24 (Suppl 1): S58-S62, 2002
9. Inzitari D, Poggesi A: Calcium channel blockers and stroke. Aging Clin Exp Res (4 Suppl):16-30, 2005
10. Korenkov A I, Pahnke J, Frei K, Warzok R, Schroeder H W S, Frick R, et al: Treatment with nimodipine or mannitol reduces programmed cell death and infarct size following focal cerebral ischemia. Neurosurg Rev 23:145-150, 2000
11. Lanterna L A, Rigoldi M, Tredici G, Biroli F, Cesana C, Gaini S M, et al: APOE influences vasospasm and cognition of non-comatose patients with subarachnoid hemorrhage. Neurology 64:1238-1244, 2005
12. Laskowitz D T, Fillit H, Yeung B, Toku K, Vitek M P: Apo-lipoprotein E-derived peptides reduce CNS inflammation: implications for therapy of neurological disease. Acta Neurol Scand 114 (Suppl 185):15-20, 2006
13. Laslo A M, Eastwood J D, Chen F X, Lee T Y: Dynamic CT perfusion imaging in subarachnoid hemorrhage-related vasospasm, AJNR Am J Neuroradiol 27:624-631, 2006

14. Leung C H S, Poon W S, Yu L M, Wong G K C, Ng H K: Apolipoprotein E genotype and outcome in aneurysmal subarachnoid hemorrhage. Stroke 33:548-552, 2002
15. Lynch J R, Wang H, Mace B, Leinenweber S, Warner D S, Bennett E R, et al: A novel therapeutic derived from apolipoprotein E reduces brain inflammation and improves outcome after closed head injury. Exp Neurol 192:109-116, 2005
16. Lynch J R, Wang H, McGirt M J, Floyd J, Friedman A H, Coon A L, et al: Simvastatin reduces vasospasm after aneurysmal subarachnoid hemorrhage: results of a pilot randomized clinical trial, Stroke 36:2024-2026, 2005
17. McCarron M O, Muir K W, Weir C J, Dyker A G, Bone I, Nicoll J A R, et al: The apolipoprotein E ε4 allele and outcome in cerebrovascular disease, Stroke 29:1882-1887, 1998
18. McGirt M J, Lynch J R, Parra A, Sheng H, Pearlstein R D, Laskowitz D T, et al: Simvastatin increases endothelial nitric oxide synthase and ameliorates cerebral vasospasm resulting from subarachnoid hemorrhage, Stroke 33:2950-2956, 2002
19. McGirt M J, Woodworth G F, Pradilla G, Legnani F, Warner D S, Tamargo R, et al: Simvastatin attenuates experimental cerebral vasospasm and ameliorates serum markers of neuronal and endothelial injury in patients after subarachnoid hemorrhage: a dose-response effect dependent on endothelial nitric oxide synthase. Clin Neurosurg 52:212-214, 2005
20. Mendelow A D: Pathophysiology of delayed ischaemic dysfunction after subarachnoid haemorrhage: experimental and clinical data, Acta Neurochir Suppl 45:7-10, 1988
21. Nosko M, Weir B, Krueger C, Cook D, Norris S, Overton T, et al: Nimodipine and chronic vasospasm in monkeys: part 1. Clinical and radiological findings. Neurosurgery 16:129-136, 1985
22. Parra A, McGirt M J, Sheng H, Laskowitz D T, Pearlstein R D, Warner D S: Mouse model of subarachnoid hemorrhage associated cerebral vasospasm: methodological analysis. Neurol Res 24:510-516, 2002
23. Petruk K C, West M, Mohr G, Weir B K, Benoit B G, Gentili F, et al: Nimodipine treatment in poor-grade aneurysm patients. Results of a multicenter double-blind placebo-controlled trial. J Neurosurg 68:505-517, 1988
24. Pickard J D, Murray G D, Illingworth R, Shaw M D, Teasdale G M, Foy P M, et al: Effect of oral nimodipine on cerebral infarction and outcome after subarachnoid hemorrhage: British aneurysm nimodipine trial. BMJ 298:636-642, 1989
25. Teasdale G M, Nicoll J A R, Murray G, Fiddes M: Association of apolipoprotein E polymorphism with outcome after head injury. Lancet 350:1069-1071, 1997
26. Yokoo N, Sheng H, Mixco J, Homi H M, Pearlstein R D, Warner D S: Intraischemic nitrous oxide alters neither neurologic nor histologic outcome: a comparison with dizocilpine. Anesth Analg 99:896-903, 2004

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

We claim:

1. A method of treating or ameliorating a cerebral hemorrhage comprising administering to a subject in need thereof a peptide compound, said peptide compound comprising a peptide consisting of less than about 50 amino acids comprising the sequence of peptide COG133 (SEQ ID NO: 1), wherein said peptide is conjugated to a PTD derived from antennapedia.

2. The method of claim 1, wherein said cerebral hemorrhage is selected from the group consisting of intraventricular hemorrhage (IVH), intracerebral hemorrhage (ICH), and subarachnoid hemorrhage (SAH).

3. The method of claim 2, wherein said subarachnoid hemorrhage is aneurismal subarachnoid hemorrhage.

4. The method of claim 1, wherein said peptide compound is administered within about 24-72 hours after subarachnoid hemorrhage has occurred.

5. The method of claim 1, wherein said peptide compound is administered within the first several weeks after subarachnoid hemorrhage has occurred.

6. The method of claim 1, wherein said peptide compound is administered at least about every 8 hours.

7. The method of claim 1, wherein said peptide compound is administered at least about every 12 hours.

8. The method of claim 1, wherein said peptide compound is administered during surgery to treat subarachnoid hemorrhage.

9. The method of claim 1, further comprising co-administering a therapeutic amount of at least one additional active agent.

10. The method of claim 9, wherein said additional active agent is a voltage-gated calcium channel inhibitor.

11. The method of claim 10, wherein said voltage-gated calcium channel inhibitor is a small molecule.

12. The method of claim 11, wherein said small molecule is nimodipine.

13. The method of claim 1, wherein said subject has suffered a cerebral vasospasm.

14. The method of claim 1, wherein said subject is at risk of a cerebral vasospasm.

15. The method of claim 1, wherein said peptide compound is a pharmaceutically acceptable salt, solvate, and/or amide.

16. The method of claim 1, wherein said peptide compound is administered orally and/or intravenously.

17. The method of claim 1, wherein one to fifteen amino acids are linked to the amino or carboxy terminus of said COG133 peptide.

18. The method of claim 1, wherein an amino acid has been inserted at the amino or carboxy terminus of said COG133 peptide.

19. The method of claim 1, wherein said PTD derived from antennapedia is RQIKIWFQNRRMKWKK (SEQ. ID. NO: 51) or RRMKWKK (SEQ. ID. NO: 52).

20. The method of claim 1, wherein said peptide compound consists of the sequence of peptide COG133 (SEQ ID NO: 1).

* * * * *